United States Patent
Kroll

(10) Patent No.: US 8,267,851 B1
(45) Date of Patent: Sep. 18, 2012

(54) METHOD AND APPARATUS FOR ELECTRICALLY GENERATING SIGNAL FOR INDUCING LUCID DREAMING

(75) Inventor: James M Kroll, Prospect Heights, IL (US)

(73) Assignee: James M Kroll, Prospect Heights, IL (US)

( * ) Notice: Subject to any disclaimer, the term of this patent is extended or adjusted under 35 U.S.C. 154(b) by 547 days.

(21) Appl. No.: 12/485,861

(22) Filed: Jun. 16, 2009

(51) Int. Cl.
*A61M 21/00* (2006.01)

(52) U.S. Cl. .......................................... 600/27; 600/26

(58) Field of Classification Search ................ 600/27, 600/26

See application file for complete search history.

(56) References Cited

U.S. PATENT DOCUMENTS

| | | | |
|---|---|---|---|
| 4,499,096 A | 2/1985 | Lotsof | |
| 4,580,570 A | 4/1986 | Sarrell et al. | |
| 4,735,199 A * | 4/1988 | DiLullo | 600/28 |
| 4,863,259 A * | 9/1989 | Schneider et al. | 351/210 |
| 5,084,007 A | 1/1992 | Malin et al. | |
| 5,306,228 A * | 4/1994 | Rubins | 600/27 |
| 5,335,657 A * | 8/1994 | Terry et al. | 607/45 |
| 5,409,445 A * | 4/1995 | Rubins | 600/27 |
| 5,507,716 A | 4/1996 | LaBerge et al. | |
| 5,540,736 A | 7/1996 | Halmovich et al. | |
| 5,551,879 A * | 9/1996 | Raynie et al. | 434/236 |
| 5,813,993 A * | 9/1998 | Kaplan et al. | 600/544 |
| 6,408,211 B1 * | 6/2002 | Powell | 607/75 |
| 6,656,137 B1 * | 12/2003 | Tyldsley et al. | 601/15 |
| 6,978,179 B1 * | 12/2005 | Flagg et al. | 607/45 |
| 2004/0266659 A1 | 12/2004 | LaBerge | |
| 2006/0136009 A1 | 6/2006 | Staffel et al. | |
| 2006/0206174 A1 * | 9/2006 | Honeycutt et al. | 607/88 |
| 2008/0109199 A1 * | 5/2008 | Conero | 703/11 |
| 2008/0304691 A1 * | 12/2008 | Lai | 381/386 |
| 2009/0207028 A1 * | 8/2009 | Kubey et al. | 340/575 |

FOREIGN PATENT DOCUMENTS

| | | |
|---|---|---|
| WO | WO-91-01756 | 2/1991 |
| WO | WO-97-18855 | 5/1997 |
| WO | WO-97-48445 | 12/1997 |
| WO | WO-99-00067 | 1/1999 |
| WO | WO-02-22203 | 3/2002 |

OTHER PUBLICATIONS

Fries P, Nikolic D, Singer W. The gamma cycle. Trends Neurosci. 2007;30:309-16.*

Lineykin, S.; Ben-Yaakov, S.; , "Unified Spice compatible model for large and small-signal envelope simulation of linear circuits excited by modulated signals," Industrial Electronics, IEEE Transactions on , vol. 53, No. 3, pp. 745-751, Jun. 2006.*

MAX038 High-Frequency Waveform Generator. Datasheet. Maxim Integrated Products, Sunnyvale, CA. 19-0266; Rev 7; Aug. 2007.*

Daniel L. Kirsch, PhD, DAAPM, FAIS and Marshall F. Gilula, M, CES in the Treatment of Insomnia—A Review and Meta-analysis—Cranial Electrotherapy Stimulation, Practical Pian Management, pp. 28-39, Oct. 2007.

Denise McKee. Cranial Electrotherapy Stimulation, Alternative and Complementary Therapies, 1(6): pp. 393-395, Nov./Dec. 1995.

\* cited by examiner

*Primary Examiner* — Charles A Marmor, II
*Assistant Examiner* — Sunita Reddy

(57) ABSTRACT

A lucid dream is induced in a subject. A brain state entrainment signal is generated in a circuit. A transducer applies a waveform of a kind sufficient to cause a lucid dream in the brain based on the brain state entrainment signal. The brain state entrainment signal modulates a carrier wave of a higher frequency than the entrainment frequency. The waveform is first applied to the subject and thereafter removed to attempt a lucid dream. The waveform can be electrical, light, sound or magnetic waveforms.

43 Claims, 20 Drawing Sheets

METHOD AND APPARATUS FOR ELECTRICALLY GENERATING SIGNAL FOR INDUCING LUCID DREAMING

BACKGROUND OF THE INVENTIONS

1. Technical Field

The present inventions relate to dream inducement and, more particularly, relate to a method and electrical apparatus for inducing lucid dreaming.

2. Description of the Related Art

A lucid dream is one in which the dreamer obtains conscious awareness while still remaining in the dream. While we are all familiar with ordinary non-lucid dreams, the notion of conscious awareness within ones dream-space is quite foreign to most. Lucid dreaming is better understood and leveraged in Eastern culture. For example, the use of lucid dreams for personal or spiritual development has been leveraged for thousands of years in Buddhist practice. In the West, most people are too busy to apply the mental training techniques required to achieve this state naturally.

Western researchers have tried to develop technological solutions in one sense or another to solve the challenge of having lucid dreams on demand. Secondary goals of such technology driven solutions have included maximizing dream vividness, recall, control or overall cognitive ability while in the dream.

The possible applications of lucid dreaming are limitless. Not surprisingly, entertainment seems to be the most common application of lucid dreaming. This might include flying like a bird, meeting up with long lost friends or even romantic fantasies. More esoteric and well known lucid dream tasks include the elimination of recurrent nightmares, practicing physical tasks and having that practice within your dream-space impact your actual wakeful performance, elimination of phobias, insights into your subconscious by engaging in conversation with dream characters and pursuing creative endeavors such as writing music or poetry under this slightly altered state of awareness.

Given the limitless number of applications for lucid dreaming, it is desired to identify a safe and predictable method for inducing lucid dreams. While lucid dream frequency is desired, it is also important to recognize that the recovery of full cognitive ability within the dream is crucial if some of the aforementioned goals are to be implemented by the dreamer.

It is known in the art that the quality of lucid dreams can vary greatly. Perhaps the single largest challenge once lucidity is obtained is the application of full cognitive ability. Lucid dreamers will often claim they were lucid, but that their cognitive ability was a fraction of what they expect when they are awake. Ramifications of this include poor ability to remember or implement goals, or an inability to remember the details of the dream once the dreamer awakens.

An early attempt at a technological solution to lucid dreaming was the concept of a lucid dream mask by LaBerge, et al in U.S. Pat. No. 5,507,716. This was essentially a facial mask worn during a lucid dream attempt. The mask has a compartment for a printed circuit board that contains a motion detector which aligns to the position of an eye. The circuit board was designed to detect rapid eye movement (REM). Upon this detection, the mask sent light or sound cues to the dreamer. These cues may manifest in the dream as light or sound anomalies. The dreamer had to train to use these cues in order to recognize that they are dreaming. The problems with these devices were several. First, most people find it difficult to sleep with a cumbersome mask strapped to their face. Second, the settings are very tricky. A little too much motion detection sensitivity and the cues can wake the dreamer before the dream is stable. Too little and the mask doesn't detect and deliver cues. Similar problems can be said of the brightness and sound settings. The worst part is that the brain becomes accustomed to this phenomenon and tends to either tune it out or wake upon light or sound stimulus. Other peculiarities can creep in such as the lucid dreamer feeling like the mask is on them during the dream leaving them unable to see. A review of various internet lucid dream sites will find few people claiming phenomenal success with such devices.

A more recent development in lucid dream induction was that provided by LaBerge in US Patent Application Publication No. 20040266659. In this application, LaBerge identified several classes of drugs that can positively impact dream lucidity and cognitive ability of the dreamer. The main focus of this development was the class of drugs known as acetylcholine esterase inhibitors. Fundamentally, these are drugs that slow the breakdown of acetylcholine in the brain. Commercial usage of drugs such as Galantamine or Huperzine-A for lucid dream induction resulted from this disclosure by LaBerge. While this class of drugs does seem to be safe and reasonably effective at lucid dream induction, they also exhibit a number of limitations. Insomnia is a common consequence of using these drugs. Not only can this leave the subject sleepy the next day, it eliminates any possibility of lucid dreaming. Since these drugs bias acetylcholine (AcH) levels, they tend to create a chemical balance that favors REM sleep over delta wave and other physically recuperative cycles of sleep. Again, this can often leave the subject run down and sleepy the next day due to a lack of recuperative sleep the prior evening. A noticeable tolerance to acetylcholine esterase inhibitors has also been exhibited and is a common problem known to those skilled in the art. A dose that used to cause a positive effect every 4th day (generally accepted as the minimal inter-use window for galantamine), can soon only realizes a positive effect once per week. Even once a week can become a challenge for users who have leveraged a drug like galantamine for a year or more. Discussion of this tolerance issue is well documented on internet based lucid dream bulletin boards. Even with the use of these AcH boosting drugs, lucid dreamers often report unsatisfactory cognitive ability and critical thinking recovery once lucid. The last and final challenge is the gastro-intestinal distress and intolerance some people realize.

Another approach to the generalized modification of brain state activity was cranial electrical stimulation (CES). Cranial electrical stimulation was researched and developed in the Soviet Union in the 1950's. At the time this application was termed "electro-sleep" because studies focused mostly on resolution of insomnia in human subjects. By the 1960's a significant amount of private and university level research was underway in the United States for both animal and human subjects. The typical applications explored during this time were reduction of pain, anxiety, depression and elimination of insomnia.

Cranial electrical stimulation differs from several other electrical or magnetic stimuli such as transcutaneous electrical nerve stimulation (TENS) or transcranial magnetic stimulation (TMS). Cranial electrical stimulation involves the delivery of a small micro current across the brain. Typically, this is delivered via electrodes clipped to the ear lobes. The currents involved are quite small, on the order of 50 $\mu$A-5 mA. Research has demonstrated that the preferred waveforms for cranial electrical stimulation applications are square or rectilinear biphasic signals with zero mean voltage delivered over time. These types of biphasic signals are easily designed and implemented to have equal positive and negative portions to eliminate the possibility of elecrolysis of the blood. This positive/negative behavior of the signal better replicates the response of nerve impulses that are characterized by having one polarity upon application of pressure and a potential of equal but opposite polarity upon release of pressure. Pulse widths of 0.1 to 2.0 seconds are commonly used and the envelope of the signal typically used for traditional applications is designed to be periodic at a rate of 0.5-3.0 Hz. It is also recognized by those skilled in the art that dynamic modification of the signal is often preferred as the brain can otherwise develop a tolerance to a repetitive electrical stimulus and slowly become unresponsive to this external signal. Methods to dynamically modify the signal include but are not limited to using on/off pulses, changing the envelope frequency over time, using a low frequency envelope to modulate a higher frequency carrier wave, changing the time domain format of the periodic signal, making changes in signal magnitude, etc.

Other cited methods are different than cranial electrical stimulation. Transcutaneous electrical nerve stimulation (TENS) for example is typically applied to injured or uncomfortable muscles and/or soft tissue areas. TENS is typically delivered in the 50-200 Hz range at much higher currents. Transcranial magnetic stimulation (TMS) differs from cranial electrical stimulation in the stimulus itself. TMS is a magnetic alteration of brain response as opposed to an electrical stimulus.

While decades of research have been implemented in this area, very little has actually been quantified in terms of how cranial electrical stimulation actually works. Most data and conclusions are empirical in nature. Blind or double blind studies routinely prove that low frequency cranial electrical stimulation in the 0.5-3.0 Hz range has positive effects in the aforementioned diseases and discomforts. Certainly it is well understood via electroencephalogram (EEG) measurements of patients before and after cranial electrical stimulation treatment that cranial electrical stimulation tends to eliminate irregular or abnormal electro chemical activity especially in the alpha range of 8-12 Hz. However the precise mechanism that drives this response is poorly understood. Most research cites the generic theory that cranial electrical stimulation helps to drive neurotransmitter balance back to a normal homeostasis. Cranial electrical stimulation regiments typically follow the model of 30 minutes of treatment per day for 5-15 days. Depending on the ailment and individual, positive response is often subjectively perceived for anywhere from 1 week to 2 years.

BRIEF DESCRIPTION OF THE DRAWINGS

The present invention is illustrated by way of example and is not limited by the accompanying figures, in which like references indicate similar elements. Elements in the figures are illustrated for simplicity and clarity and have not necessarily been drawn to scale.

The details of the preferred embodiments will be more readily understood from the following detailed description when read in conjunction with the accompanying drawings wherein.

DETAILED DESCRIPTION OF THE PREFERRED EMBODIMENTS

Figure 1:
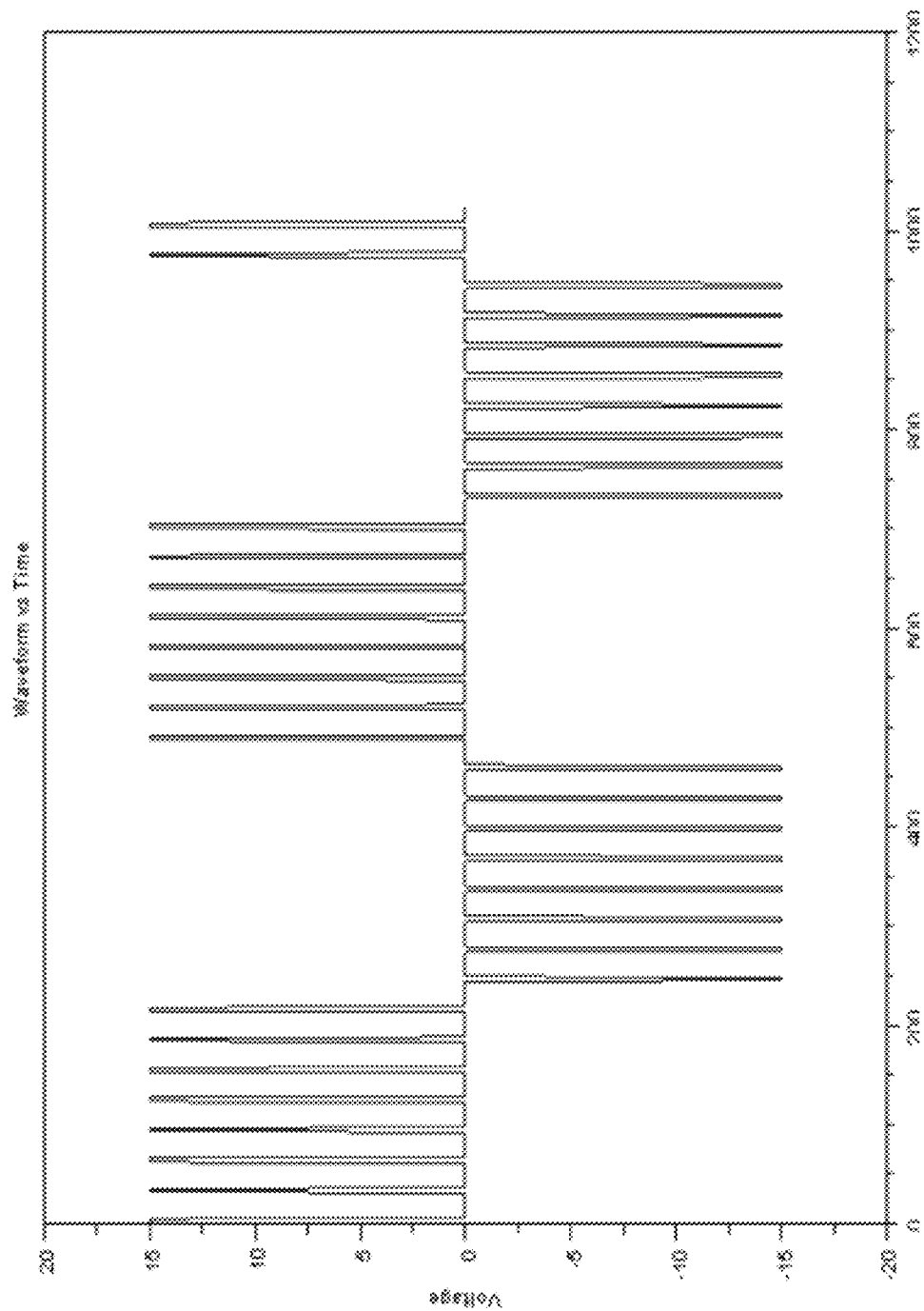
FIG. 1 illustrates a trace of a preferred cranial electrical stimulation waveform according to the present inventions.

A lucid dream induction method that is both effective and safe is highly desired. The effectiveness of the method is gauged in terms of probability of lucid dream induction as well as overall quality (vividness, recall, control). Other considerations come directly into play such as the dreamer's ability to recover full cognitive ability, which in turn can facilitate a wider range of tasks and challenges the dreamer can enjoy. Finally, the lucid dream induction method should ideally have no tolerance with itself from night to night or cross-tolerance with known lucid dream methods. Unpleasant side effects such as insomnia or poor physically recuperative sleep should be minimal or non-existent.

The present inventions involve the application of a cranial electrical stimulation signal with specific spectral characteristics. These signal properties were previously unexplored in both the lucid dream field and the cranial electrical stimulation field of study. A period of time is identified for generation of a brain state entrainment signal. This entrainment period involves the short term application of the brain state entrainment signal via a transducer which converts the circuits electrical signal to a waveform suitable for transmission across the subjects cranium. The entrainment period is preferably aligned with the natural sleep cycle such that removal of the device and re-entry into sleep is highly likely to align with a natural REM period of the sleep cycle. Other techniques such as wake back to bed (WBTB) may be applied before the entrainment period. WBTB is well understood by those skilled in lucid dream techniques. Based on empirical data, the period from 5 minutes to 60 minutes after removal of the device is a period of high lucid dream probability. The brain state entrainment signal effectively primes the brain for this state characterized by improved logical thinking within ones dream-space. This improved logical ability has the effect of allowing the dreamer to identify odd or impossible elements in their dream and hence conclude they are dreaming. It also improves the dreamer's ability to remember and implement complex lucid dream tasks and goals.

The relationship suggested by the empirical data suggests additional features which would be of interest to include in a self contained cranial electrical stimulation device that is capable of delivering the lucid dream inducing brain state entrainment signal. These features include a vibrational alarm and an on/off cycle mode to create a cyclic pattern of entrainment and optimized lucid dream windows.

While the empirical data thus far has been obtained via a very specific cranial electrical stimulation waveform, other waveforms which have similar frequency domain characteristics are potential candidates for cranial electrical stimulation induction of lucid dreams. These waveforms will be explored and patent protection will be claimed by way of definition of the ratio metric characteristics of the spectral response.

While a preferred usage protocol is defined for lucid dream induction via cranial electrical stimulation, several other usage variations exist and will be defined.

FIG. 1 illustrates the time domain capture of one example of a preferred cranial electrical stimulation waveform at 19.2K samples/second. In one embodiment a biphasic rectilinear waveform is used as the preferred cranial electrical stimulation waveform. Mathematically, this signal is the multiplication of two signals in the time domain. The first is a rectified 632 Hz square wave pulse train of duty cycle 15%. Each pulse in this train is (1/632)*0.15≈0.23734177 mS in duration. This train is modulated by a 39.5 Hz continuous biphasic brain state entrainment signal. Mathematically, this signal may be represented in the continuous time domain as follows:

$$CES_{pref}(t) = 15 \Sigma_{n=0}^{\infty} [1-2U(n \bmod 16-8)][U(t-n/632)-U(t-(n+0.15)/632)]$$

Equation 1

Here U(t) is the unit step function (value of +1 for all arguments t>=0 and 0 otherwise) and the mod_16 operation over the index n yields the integer remainder for the operation n divided by 16.

Figure 2:
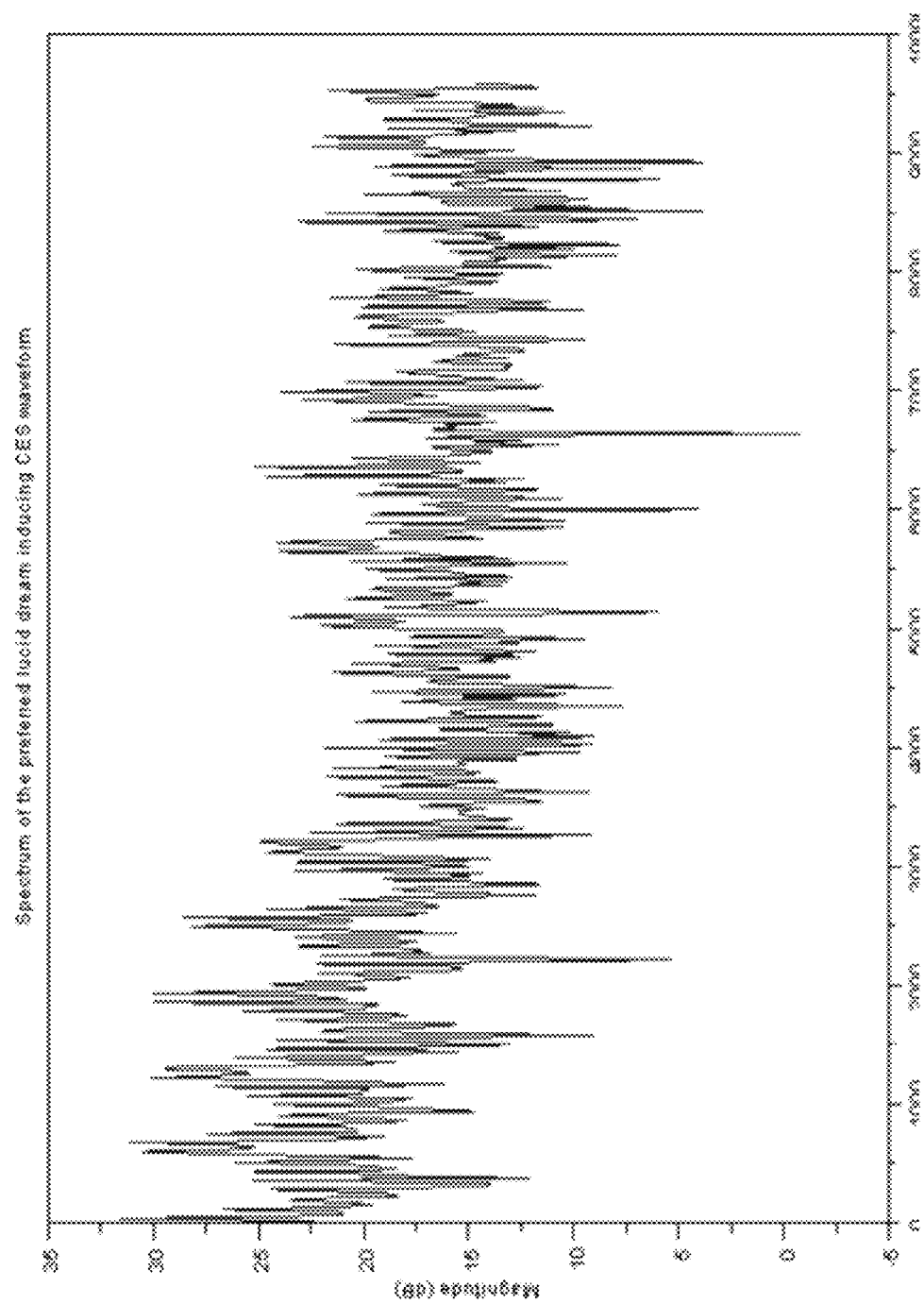
FIG. 2 illustrates a trace of a spectrum of a preferred lucid dream inducing cranial electrical stimulation waveform according to the present inventions.

FIG. 2 illustrates a trace of the frequency domain characteristics of a preferred lucid dream inducing cranial electrical stimulation waveform. The spectral response of this waveform was determined via Fast Fourier Transform analysis on a 1024 point signal capture utilizing a sampling frequency of 19.2K samples/second. This spectral plot agrees with theoretical analysis. Since the cranial electrical stimulation waveform in question is the multiplication of two simple time domain signals, the frequency response is the mathematical convolution of the individual frequency responses of the component signals. The primary response centered at 39.5 Hz is a result of the 39.5 Hz continuous biphasic brain state entrainment signal and resulting composite signal envelope. The aliases at multiples of 632+/−39.5 Hz are a consequence of basic sampling theorem and Fourier analysis.

Figure 3:
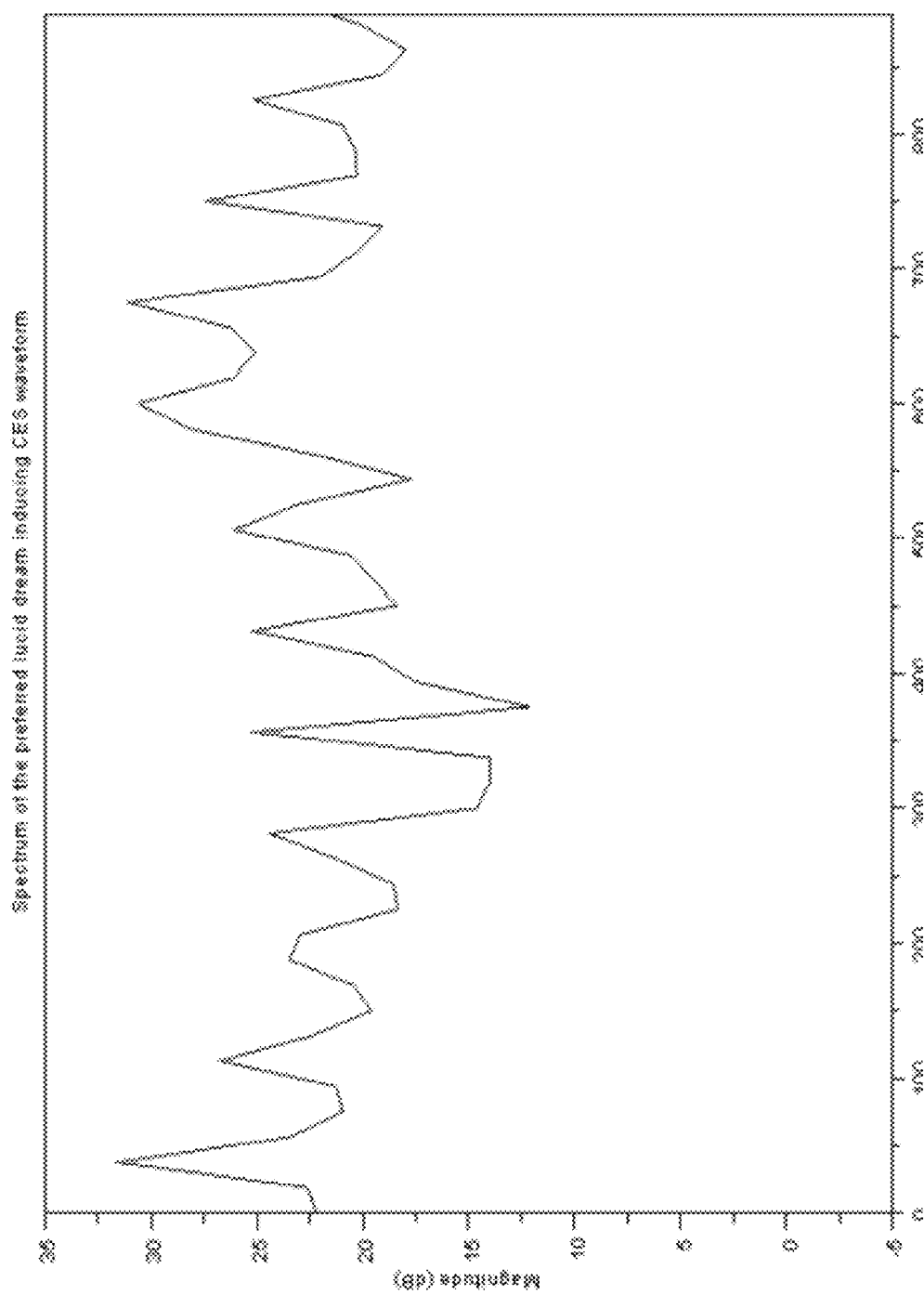
FIG. 3 illustrates a trace of a spectrum of the preferred lucid dream inducing cranial electrical stimulation waveform according to the present inventions.

FIG. 3 illustrates a trace of a spectrum of the preferred lucid dream inducing cranial electrical stimulation waveform (low band). FIG. 3 is a close-up of the low band frequency response which better illustrates the peaks at 39.5 Hz, 592.5 Hz and 671.5 Hz. The spectral response at 39.5 Hz is believed to be the key to high level lucid dream induction. The properties of the proposed cranial electrical stimulation waveform were chosen to affect natural signal patterns in the brain associated with awareness, logical thinking and problem solving. Energy at 39.5 Hz may be detected during wakeful hours and REM sleep. This energy is generally absent during non-REM and completely absent if the subject is under general anesthesia. Furthermore, activity in this range can be more pronounced during complex problem solving and application of logical thinking. It is this logical thinking that seems to be "turned off" during non-lucid dreams. It appears that this logical thinking can be stimulated by the application of a suitably chosen brain state entrainment signal. In practice, this electro chemical signature associated with awareness and logical thinking can be measured to be in the range of 38.8 to 40.1 Hz, depending on the physical measurement points across the cranium. Such measurements may be obtained via a standard EEG. It can be hypothesized that an externally introduced brain state entrainment signal in the range of 39.5+/−2 Hz should have an effect on this natural 39.5 Hz brain state signature. The brain state entrainment signal can have a frequency in a range of about 34.5 Hz to about 44.5 Hz or more specifically the brain state entrainment signal can have a frequency in a range of about 37.5 Hz to about 41.5 Hz.

In a preferred embodiment of this new lucid dream induction method the sleeper awakens after 5-6 hours of sleep and undergoes 30 minutes of wakeful time allowing AcH levels to rise naturally. The cranial electrical stimulation waveform is applied at the prescribed frequencies and the user relaxes and attempts to fall asleep. Sleep is not considered to be challenging during this process and users most commonly report light non-REM sleep during the entrainment phase. Dream lucidity is sometimes reported during the entrainment phase (only 10% of the time given data collected thus far). Upon awakening (or if sleep is not achieved, after a minimum of 45 minutes of entrainment) the user removes the device, reviews their intention to become lucid as well as their lucid goals and resumes sleep. The period from 5-60 minutes after removal of the device appears to be an optimized lucid dream window. Users report elevated awareness and rather immediate lucidity via the dream initiated lucid dream (DILD) technique having had the cranial electrical waveform effectively "prime" the brain for dream lucidity.

While the traditional technique of wake back to bed is discussed above, users of this CES lucid dream inducing technology have reported successful lucid events without WBTB and as late as 2-3 hours after removal of the device.

Users have reported wake initiated lucid dreams (passing into ones dream-space without a break in conscious awareness) but these appear to be less common via this technology.

It is important to understand the timing of the entrainment and alignment with the natural sleep cycle. The human sleep cycle is approximately 90 minutes long. Roughly speaking, REM sleep is the final phase of each of these 90 minute windows. It is generally accepted that most vivid dreams occur in our REM cycles. It is also well known that our time in REM increases monotonically as the evening progresses. This is conceptually demonstrated in FIG. 4.

Figure 4:
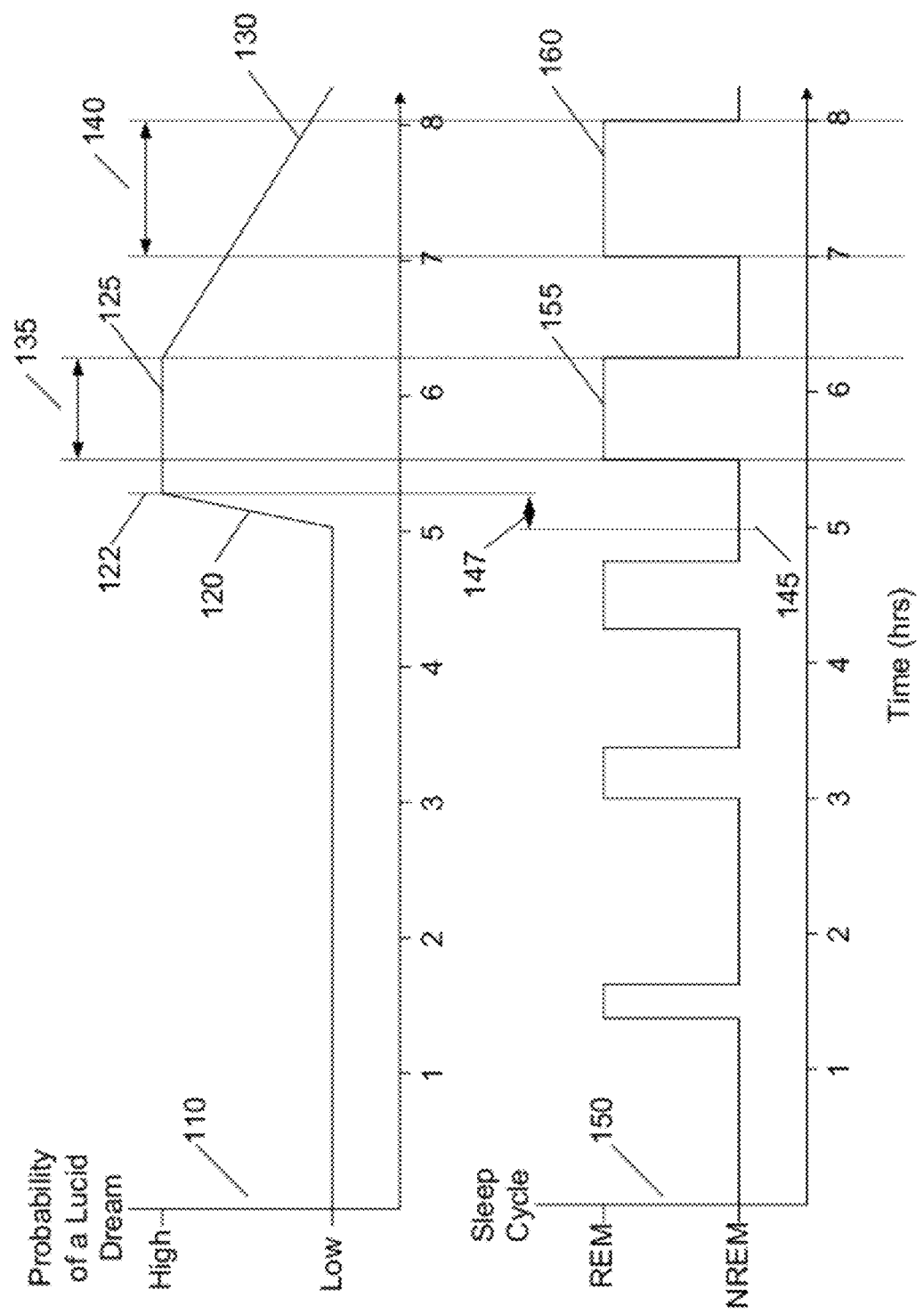
FIG. 4 illustrates two timing diagrams of an example sleep cycle and suggested alignment with an optimized lucid dream window according to the present inventions.

FIG. 4 illustrates two timing diagrams of an example sleep cycle and suggested alignment with an optimized lucid dream window. In the lower portion 150 of FIG. 4, the time in REM and non-REM (NREM) is tracked over time. The synchronized graph 110 above assumes the user wakes after 5 hours 145, applies the device and falls asleep approximately 45 minutes later. When sleep resumes, another 15 minutes of the brain state entrainment phase are used up in NREM 147 before removing the cranial electrical stimulation device 122. Hence the user has applied the cranial electrical stimulation waveform for a total of 60 minutes before removal. The ramp up in lucid dream probability 120 in the top figure represents the increased probability of a lucid dream while wearing the device (assuming it aligns with a REM period). It is presumed that the optimized lucid dream window 125 lasts 60 minutes after removal of the device and has a slow ramp down 130 over the next two hours. Notice how the 60 minute optimized lucid dream window 125 has been aligned with the significantly long 4$^{th}$ REM cycle 155 as shown by the time 135 delineated by dotted vertical lines. Additionally, there is an increased lucid dream probability 140 which spills into the 5$^{th}$ REM cycle 160 as well.

Since the preferred method of using cranial electrical stimulation to induce lucid dreams involves the application of the device after several hours of sleep, it is envisioned that a lucid dream inducing cranial electrical stimulation device would support an alarm. One realization of this could be a vibrational alarm. This would actually serve several purposes. First, a small clip on vibrating alarm would not wake a spouse or anyone else within listening range of ones bed. The first application would be to simply wake the sleeper at an appropriate time in their sleep cycle in order to prepare the electrodes with saline or electro-conductive gel and configure the device. For example, this one shot alarm might be configurable from 1-8 hours in 15 minute increments. This is demonstrated by the left most arrow 220 in FIG. 5.

Figure 5:
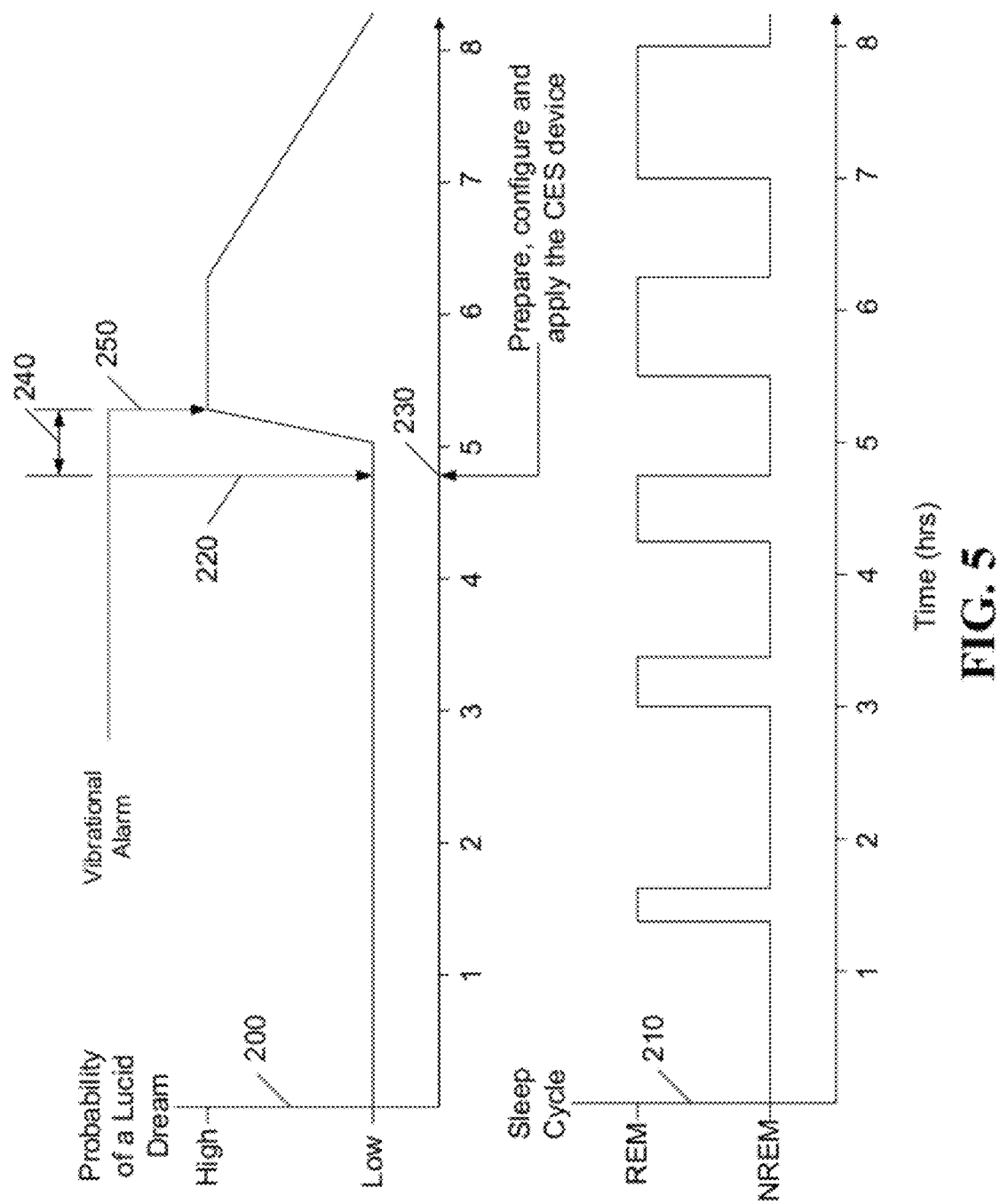
FIG. 5 illustrates two timing diagrams of an application of an alarm such as a vibrational alarm to wake the sleeper for initial cranial electrical stimulation application as well as right before the optimized lucid dream window according to the present inventions.

FIG. 5 illustrates two synchronized timing diagrams 200 and 210 of an application of an alarm such as a vibrational alarm to wake the sleeper for initial cranial electrical stimulation application as well as right before the optimized lucid dream window for purposes of reviewing lucid intentions. Here it is assumed that the alarm wakes the sleeper approximately 4.75 hours into their sleep cycle 220 for purposes of device preparation 230.

Once the person has prepared the device they are likely to want to go back to sleep while the cranial electrical stimulation device is in a brain state entrainment mode and in the process of opening an optimized lucid dream window. In practice, it makes sense to wake the sleeper right before the brain has been sufficiently prepared to lucid dream. Endless entrainment is presumed to be wasteful. Additionally, it is helpful to regain conscious awareness and review goals right before attempting to lucid dream. Again, a one shot alarm as described above could serve this purpose quiet well. This is described in FIG. 5 where it is assumed the user prepares and applies the device 230, stays up for 30 minutes (hence no progression in the sleep cycle timing diagram) and then sets the alarm for 30 minutes 240. The total entrainment time would then be 60 minutes at which time the alarm goes off to wake the sleeper as per the right most arrow 250 in FIG. 5. This is an appropriate time to remove the device, review intentions and attempt to lucid dream.

The final generalization flows from the observation that one can potentially benefit from a cyclic mode of brain state entrainment. Such a mode would cycle on and off with the intention of extending the time duration of high lucid dream probability. Consider such a mode to have an on configuration of 1 to 120 minutes in 1 minute increments with a default setting of 60 minutes. The off mode would have an independent configuration with the same supported time periods and default. One can envision a mode where the user prepares the device and configures the cyclic mode to cycle at 30 minutes on and 60 minutes off. This would have the effect of priming the brain for lucid dreaming periodically and thus extending the theoretical timeframes for high lucid dream probability. This is described in FIG. 6.

Figure 6:
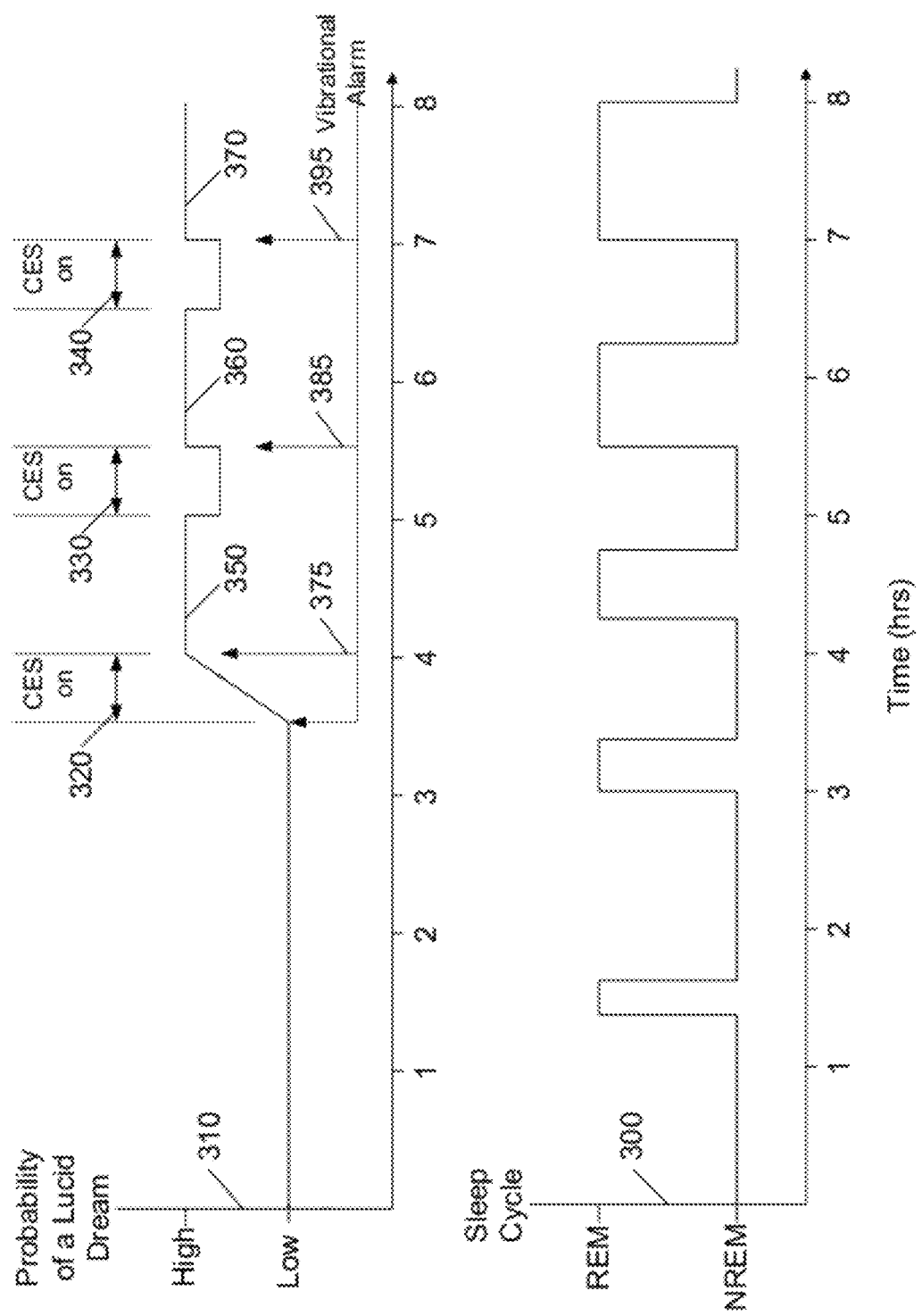
FIG. 6 illustrates two timing diagrams of a cyclic on/off mode and vibrational alarm support to periodically open optimized lucid dream windows and wake the dreamer prior to the start of such events according to the present inventions.

FIG. 6 illustrates two synchronized timing diagrams 300 and 310 of a cyclic on/off mode and vibrational alarm support to periodically open optimized lucid dream windows and wake the dreamer prior to the start of such events. Here it is assumed that an elevated likelihood of dream lucidity is realized during the 30 minute brain state entrainment phases 320, 330 and 340 but that it is not as high as when the entrainment is in any of the 60 minute off cycles 350, 360 and 370 which represent the cyclic train of optimized lucid dream windows.

A final supporting feature in cyclic mode would be the application of a cyclic vibrational alarm. As per the diagram in FIG. 6, the vibrational alarm in cyclic mode would automatically go off at the beginning of each cranial electrical stimulation off phase 375, 385 and 395. Much like the concept before, this awakening gives the user time to reflect on lucid intentions and goals right before resuming sleep in an optimized lucid dream window. Enabling the cyclic vibrational alarm would be a sub-option if the cyclic mode for cranial electrical stimulation is enabled.

Signal Generalizations and Ratio Metric Qualification of Lucid Dream Inducing Signals As discussed in the cranial electrical stimulation overview section, there are many different types of cranial electrical stimulation waveforms used in practice. The main design criterion is that the signal voltage is zero mean over time. Here, we will present several variations on cranial electrical stimulation waveforms that would be expected to have lucid dream inducing properties. Since the human head is a non-uniform transmission medium, it is likely that significant cranial electrical stimulation waveform distortion will occur if measured at arbitrary positions within the cranium. As such it is hypothesized that the specific time domain properties of a cranial electrical stimulation waveform are less important than its spectral characteristics delivered over time. These spectral characteristics are dominated by the biphasic aspect of the signal envelope. In practice, the spectral properties of this envelope are designed to be in the predominant range of electro chemical activity of the human brain. It is further noted in the cranial electrical stimulation literature that dynamic variation of the cranial electrical stimulation waveform can be beneficial, as the brain will have more difficulty staying in its steady state electro chemical condition. Stated reciprocally, more dynamic signals may be more effective at modifying electrical activity in the brain. With these considerations, let us consider several variations of the lucid dream inducing signal defined in Equation 1.

Figure 7:
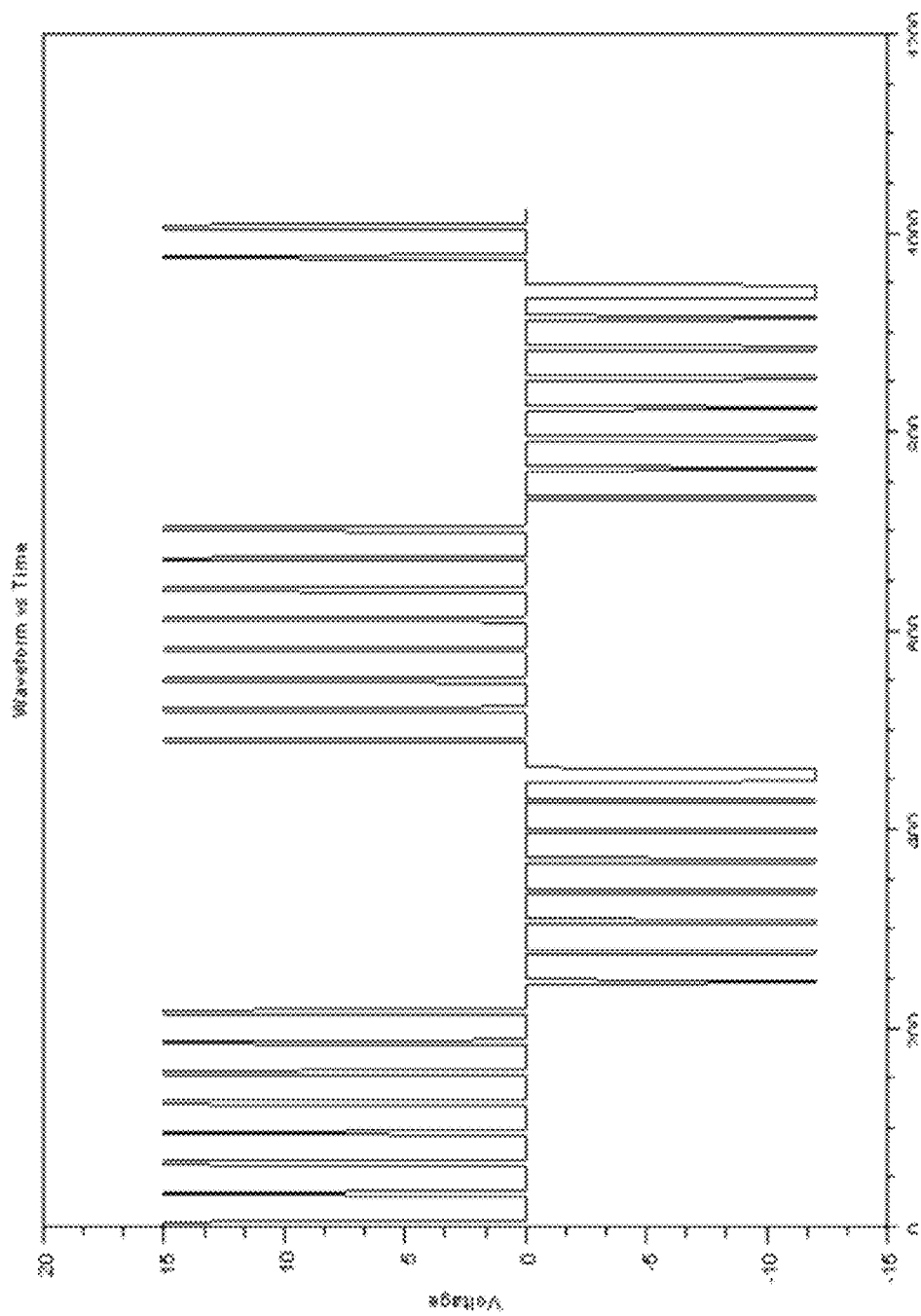
FIG. 7 illustrates a trace of an asymmetric multi-modulated cranial electrical stimulation waveform according to the present inventions.

FIG. 7 displays a time domain capture of an asymmetric multi-modulated waveform with signal envelope of 39.5 Hz taken at 19.2K samples/second. This is essentially the signal of Equation 1 but with +15V and −12V peak voltages. To maintain a zero voltage over time, the carrier is perturbed at the tail end of the negative envelope in order to lock the waveform voltage at −12 volts for a period of time sufficient to cancel the positive voltage bias earlier in the cycle and insure a zero voltage delivery over time.

Figure 8:
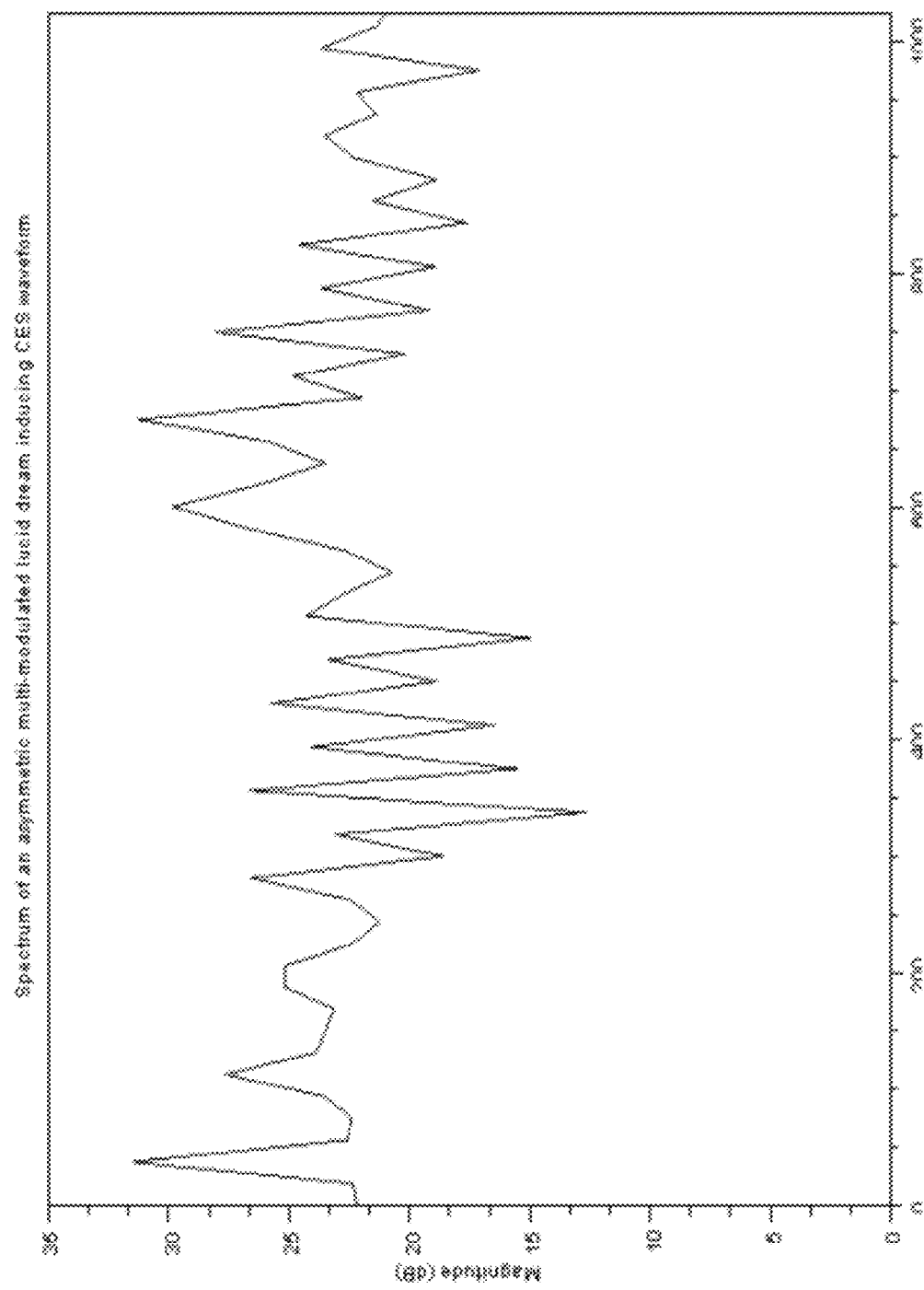
FIG. 8 illustrates a trace of the spectrum of an asymmetric multi-modulated lucid dream inducing cranial electrical stimulation waveform according to the present inventions.

FIG. 8 illustrates a trace of the frequency response of this waveform—the spectrum of an asymmetric multi-modulated lucid dream inducing cranial electrical stimulation waveform. As expected, this is quite similar to the spectral plot of the waveform associated with Equation 1. The frequency response of this waveform between 0-100 Hz is dominated by a spectral peak at 39.5 Hz.

Figure 9:
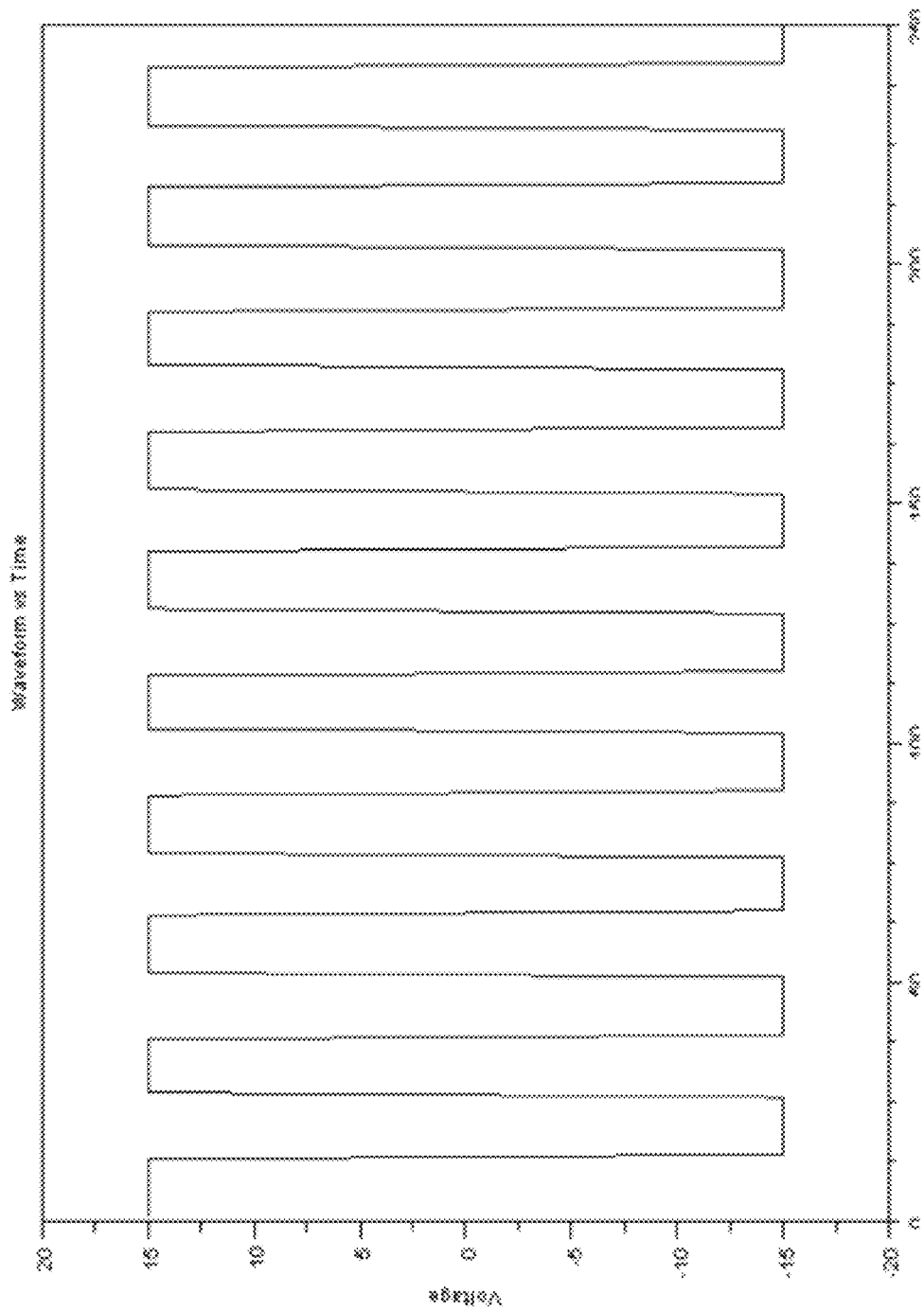
FIG. 9 illustrates a trace of a square waveform for lucid dream induction according to the present inventions.

FIG. 9 illustrates a trace of a +/−15 V square waveform with 100% duty cycle for lucid dream induction. This is a simple square wave at 39.5 Hz. This waveform has peak voltages of +/−15V. Since it is a continuous waveform which never locks out at 0 V it has an effective duty cycle of 100%. The spectral response of this waveform is shown in FIG. 10.

Figure 10:
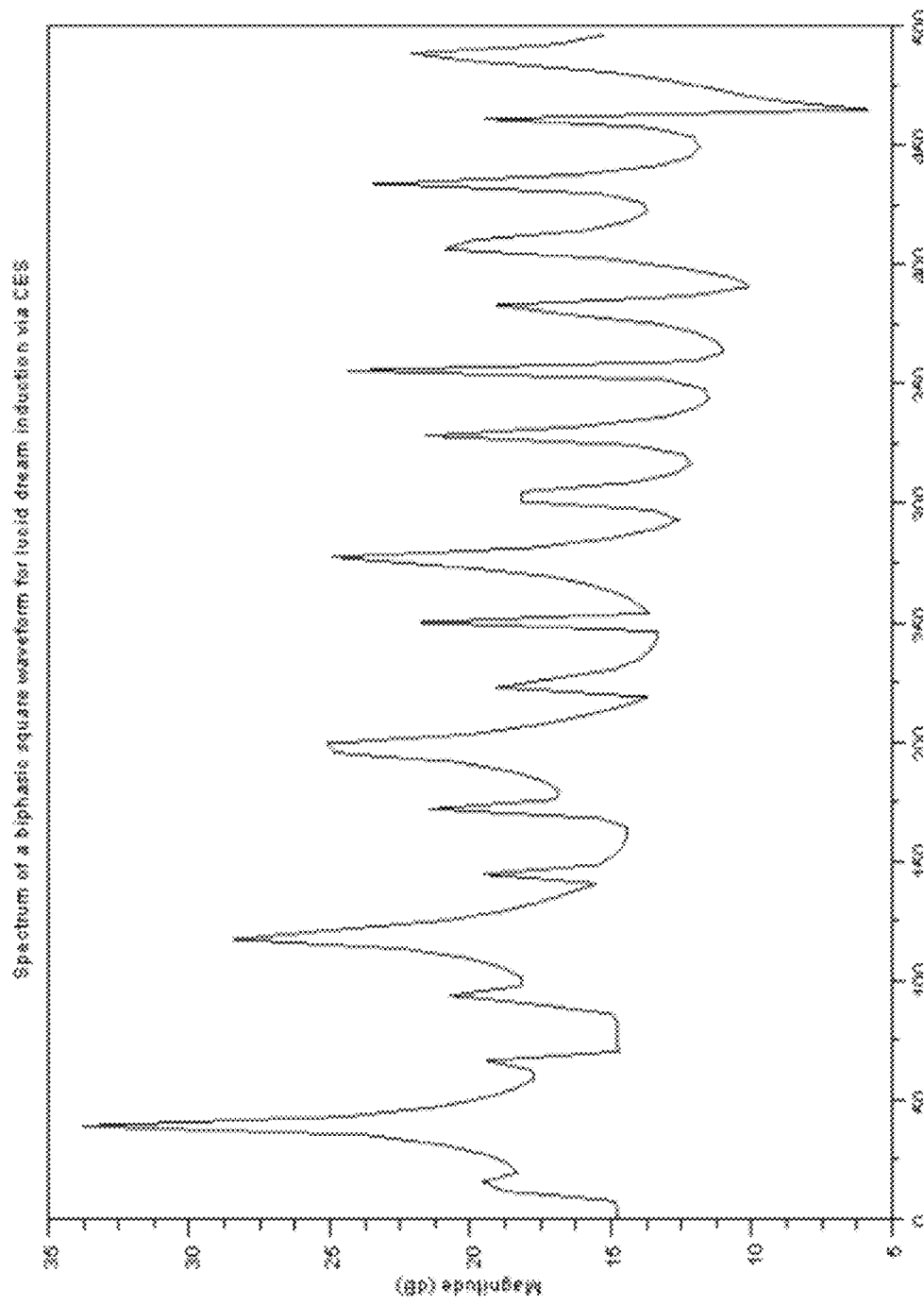
FIG. 10 illustrates a trace of the spectrum of a square waveform for lucid dream induction according to the present inventions.

FIG. 10 illustrates a trace of the spectrum of a square waveform with 100% duty cycle for lucid dream induction. As one would expect, there is a sharp peak at 39.5 Hz. Again, this is the aspect of the spectrum that dominates from 0-100 Hz.

Figure 11:
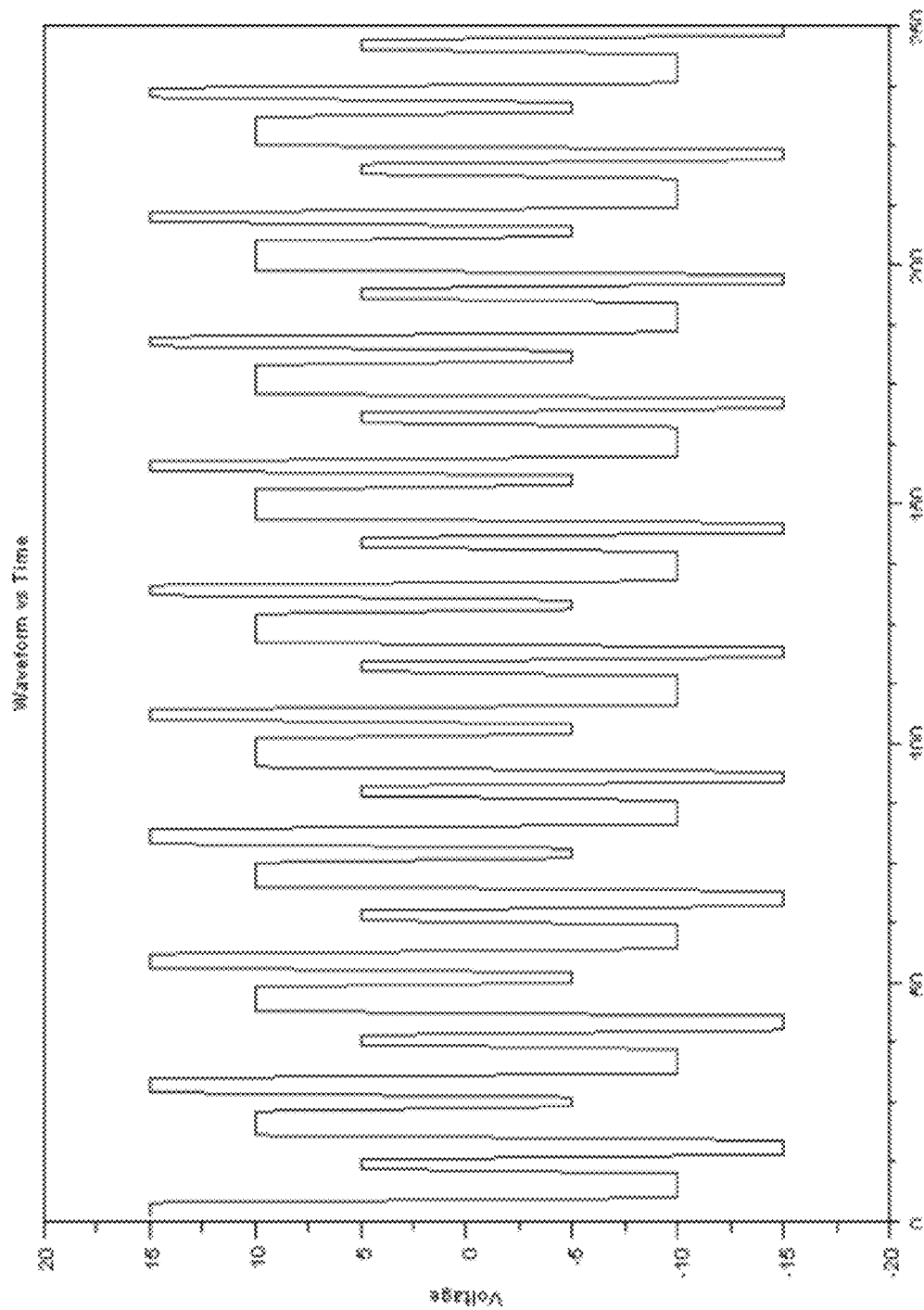
FIG. 11 illustrates a trace of a biphasic signal modulating a non-uniform carrier for lucid dream induction according to the present inventions.

FIG. 11 illustrates a trace of a biphasic brain state entrainment signal modulating a non-uniform carrier with 100% duty cycle for lucid dream induction. The resulting signal is a bipolar asymmetric rectilinear waveform. FIG. 11 is the resulting composite waveform. Essentially, this is a biphasic 39.5 Hz square wave multiplied by a multi-level higher frequency carrier. The carrier is effectively 3 times faster than the signal envelope and is irregular in both magnitude and duration of the pulses.

Figure 12:
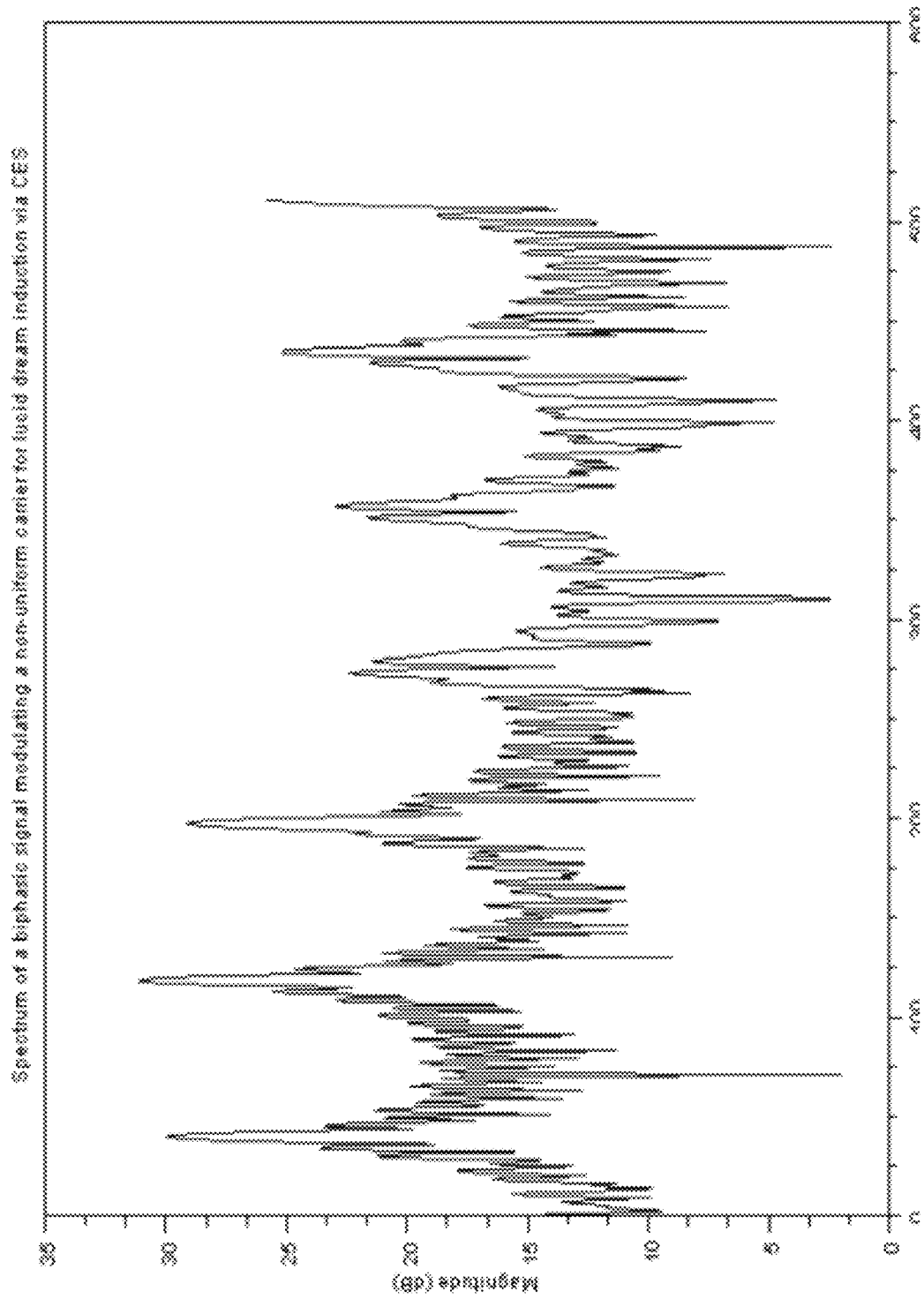
FIG. 12 illustrates a trace of the spectrum of a biphasic signal modulating a non-uniform carrier for lucid dream induction according to the present inventions.

FIG. 12 illustrates a trace of the spectrum of a biphasic signal modulating a non-uniform carrier with 100% duty cycle for lucid dream induction. FIG. 12 demonstrates the spectral response of this potential cranial electrical stimulation waveform. As expected, there are spectral peaks at both 39.5 Hz and approximately 118.5 Hz.

Figure 13:
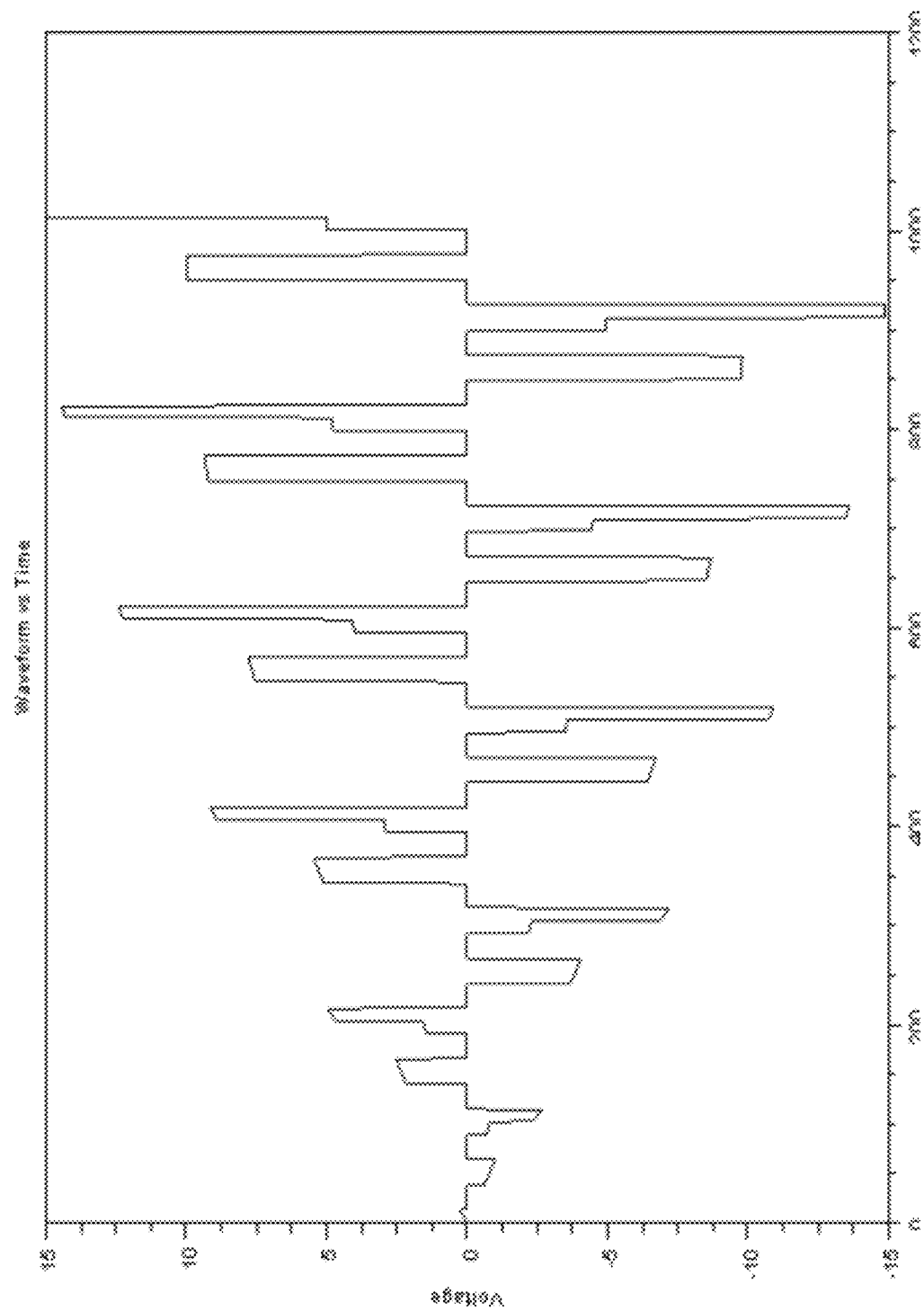
FIG. 13 illustrates a trace of an example of a cranial electrical stimulation waveform according to the present inventions.

FIG. 13 illustrates a trace of a cranial electrical stimulation waveform, multi-level carrier with 50% duty cycle and sine wave amplitude modulation at 2 Hz. This final example is another composite waveform where we start with a 39.5 Hz square wave. This is multiplied by a carrier that has periodic but irregular magnitude and pulse durations with 50% duty cycle. The carrier is running at a frequency 3 times greater than the 39.5 Hz square wave. The signal is then modulated by a continuous sine wave at 2 Hz. This is a very dynamic waveform in the time domain, but in the frequency domain we would expect peaks at 39.5 Hz and 118.5 Hz.

Figure 14:
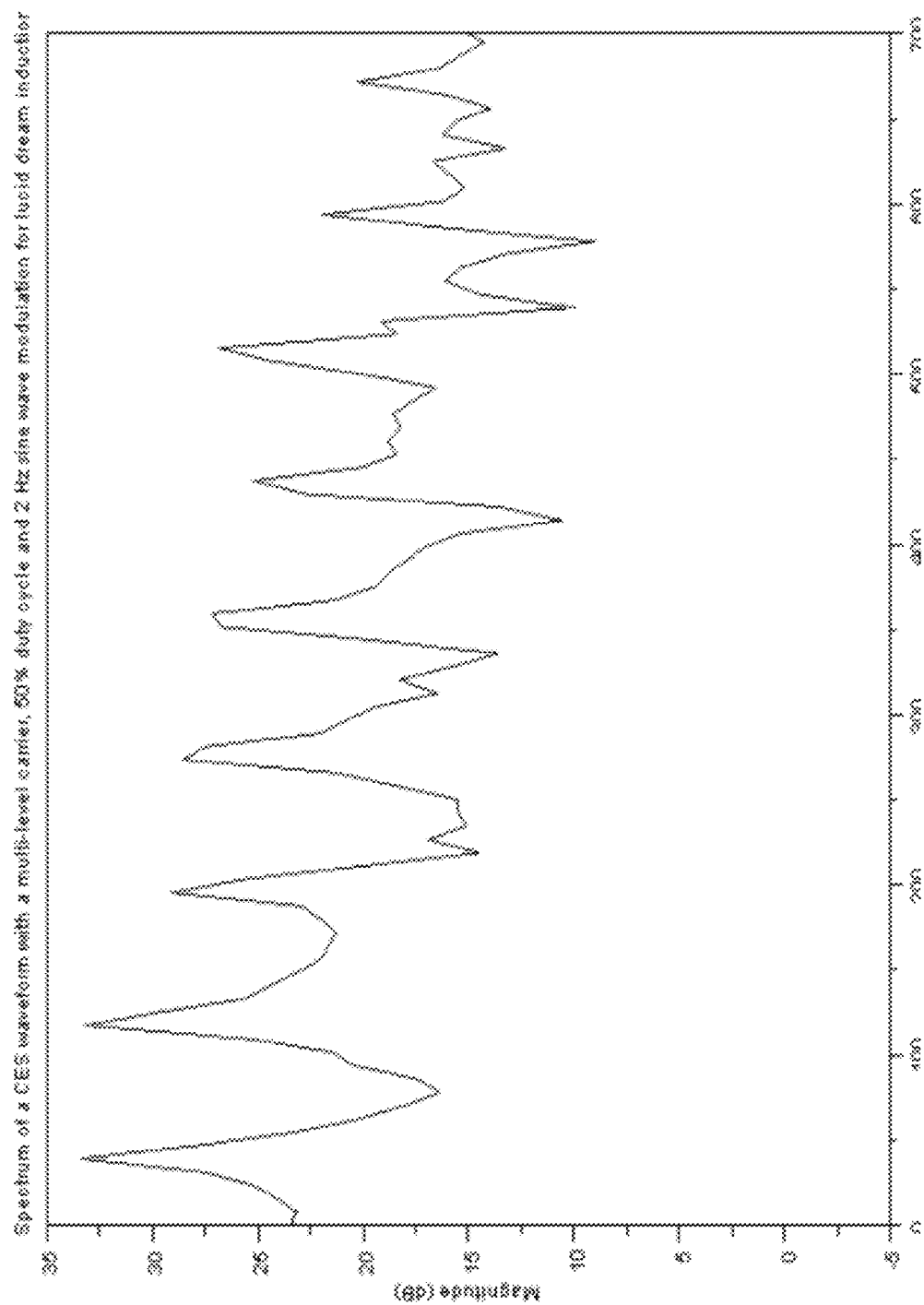
FIG. 14 illustrates a trace of the spectrum of one other example of a cranial electrical stimulation waveform according to the present inventions.

FIG. 14 illustrates a trace of the spectrum of the cranial electrical stimulation waveform with multi-level carrier and 50% duty with sine wave modulation at 2 Hz. The low frequency response of this resulting waveform is illustrated and demonstrates the expected peaks. Note the expected component at 2 Hz is not visible as the plot is over 512 samples at 8K samples/second. Hence the signal is not long enough to demonstrate a 2 Hz component in the Fast Fourier Transform calculation.

The conclusion from these examples is that there are many ways to generate valid cranial electrical stimulation waveforms that are dynamic in nature and have spectral properties conducive to lucid dream induction. Other examples might include a continuous frequency modulation by periodically modifying the pulse duration of the envelope, on/off pulses over time (e.g. one second on, one second off) and so forth. In order to define generalized lucid dream inducing signal criteria, it makes more sense to turn to the frequency domain characteristics of these waveforms.

Define the following waveform:

$$x_{nT}(t) = CES_{ld}(t)[U(t-nT) - U(t-(n+1)T)]$$

where $CES_{ld}(t)$ is a cranial electrical stimulation waveform with possible lucid dream induction properties, n is a positive or negative integer and t is continuous time. Hence $x_{nT}(t)$ is the $n^{th}$ segment of a waveform $CES_{ld}(t)$ where all waveform amplitude outside the time range of the segment [nT: (n+1)T] seconds is set to zero.

Let the Fourier transform of this waveform be defined as:

$$X_{nT}(\omega) = \int_{-\infty}^{\infty} x_{nT}(t)e^{-j\omega t}dt = \int_{-\infty}^{\infty} x_{nT}(t)e^{-j2\Pi ft}dt$$

Define two ratio metric energy tests as follows:

$$M_1(nT) = [\int_{(2\Pi*34.5)}^{(2\Pi*44.5)} |X_{nT}(\omega)|^2 d\omega] / [\int_{(2\Pi*20)}^{(2\Pi*100)} |X_{nT}(\omega)|^2 d\omega]$$

$$M_2(nT) = [\int_{(2\Pi*34.5)}^{(2\Pi*44.5)} |X_{nT}(\omega)|^2 d\omega] / [\int_{0}^{(2\Pi*100)} |X_{nT}(\omega)|^2 d\omega]$$

A waveform $CES_{ld}(t)$ will be considered to have lucid dream inducing properties if the following criterion is true:

Equation 2: Metric to Define a Lucid Dream Inducing Waveform $$M_1(n*0.1) > 0.25 \text{ OR } M_2(n*4) > 0.2$$

for any integer n in the range −∞<n<∞.

Let us consider the implementation of this test and the criteria in question. What this suggests is that a waveform $CES_{ld}(t)$ is analyzed recursively. On the first pass over time, the waveform is partitioned into contiguous segments of duration 0.1 seconds. For each 0.1 second window, the waveforms Fourier Transform is calculated and the energy in the band from 34.5 Hz<f<44.5 Hz is compared to the energy in the band from 20 Hz<f<100 Hz. Since the window duration is 0.1 seconds, a 20 Hz waveform component has two cycles within this window and will certainly show in the Fourier Transform calculation. If the time domain waveform was nothing but white noise in such a time window, then we would expect $M_1(n*0.1) \approx 10/80 = 0.125$. A metric of twice that level (or 0.25) is considered to be a significant bias in the lucid dream inducing frequency range. The positive detection of $M_1(n*0.1) \geq 0.25$ for any n would be enough to logically conclude that the waveform was designed for lucid dream induction.

If no such lucid dream inducing components are found over the 0.1 second windows, then a recursive pass is made over all contiguous time windows of duration 4 seconds. Similar to before, metric $M_2(n*4)$ will include spectral components as low as 0.5 Hz as each such waveform component will oscillate twice within that 4 second window. Again, if the time domain waveform was nothing but white noise in this range, then we would expect $M_2(n*4) \approx 10/100 = 0.1$. As stated before, a metric of twice that level (or 0.2) is considered to be a significant bias in the lucid dream inducing frequency range. The positive detection of $M_2(n*4) \geq 0.2$ for any n would be enough to logically conclude that the waveform was designed for lucid dream induction.

Generalizations for the Timing and Use Protocols for Cranial Electrical Stimulation Induction of Lucid Dreams Two example generalizations of the usage of cranial electrical stimulation lucid dream inducing waveforms will be presented. These are beyond the prescribed optimal usage discussed herein.

A first generalization is the use of cranial electrical stimulation prior to starting ones sleep cycle. One can easily envision applying the cranial electrical stimulation waveform prior to retiring for the evening. Sleep may or may not be achieved within this time period. However, the brain would effectively be primed for dream lucidity once the device is halted. Such a period would be expected to last 1-3 hours after removal of the device. While this period does not align with long REM cycles, there would be some intersection and hence improved possibility of lucid dreaming. The cycle on/off mode could also be applied which would lengthen the optimized lucid dream window created.

A second generalization of interest is a protocol more in line with traditional cranial electrical stimulation usage. For example, the lucid dream enthusiast might apply cranial electrical stimulation for 30-60 minutes per day for some number of consecutive days (e.g. 1 week straight). Since cranial electrical stimulation applied in this fashion at low band frequencies has been shown to have a prolonged effect consistent with the short term brain state changes, it could be expected that a cranial electrical stimulation waveform designed according to Equation 2 would exhibit a similar longer term positive impact to lucid dreaming if used in this manner. In fact, early empirical data confirms this hypothesis.

Exemplary embodiments of the implementation in a device will be discussed. There are many ways to implement a device that provides one or more of the signals and features discussed. Here, several options will be presented from a simple amplifier circuit being driven from an externally generated signal to more sophisticated self contained micro processor based solutions.

Simple PC Based wav File Driving an Amplifier

Figure 15:
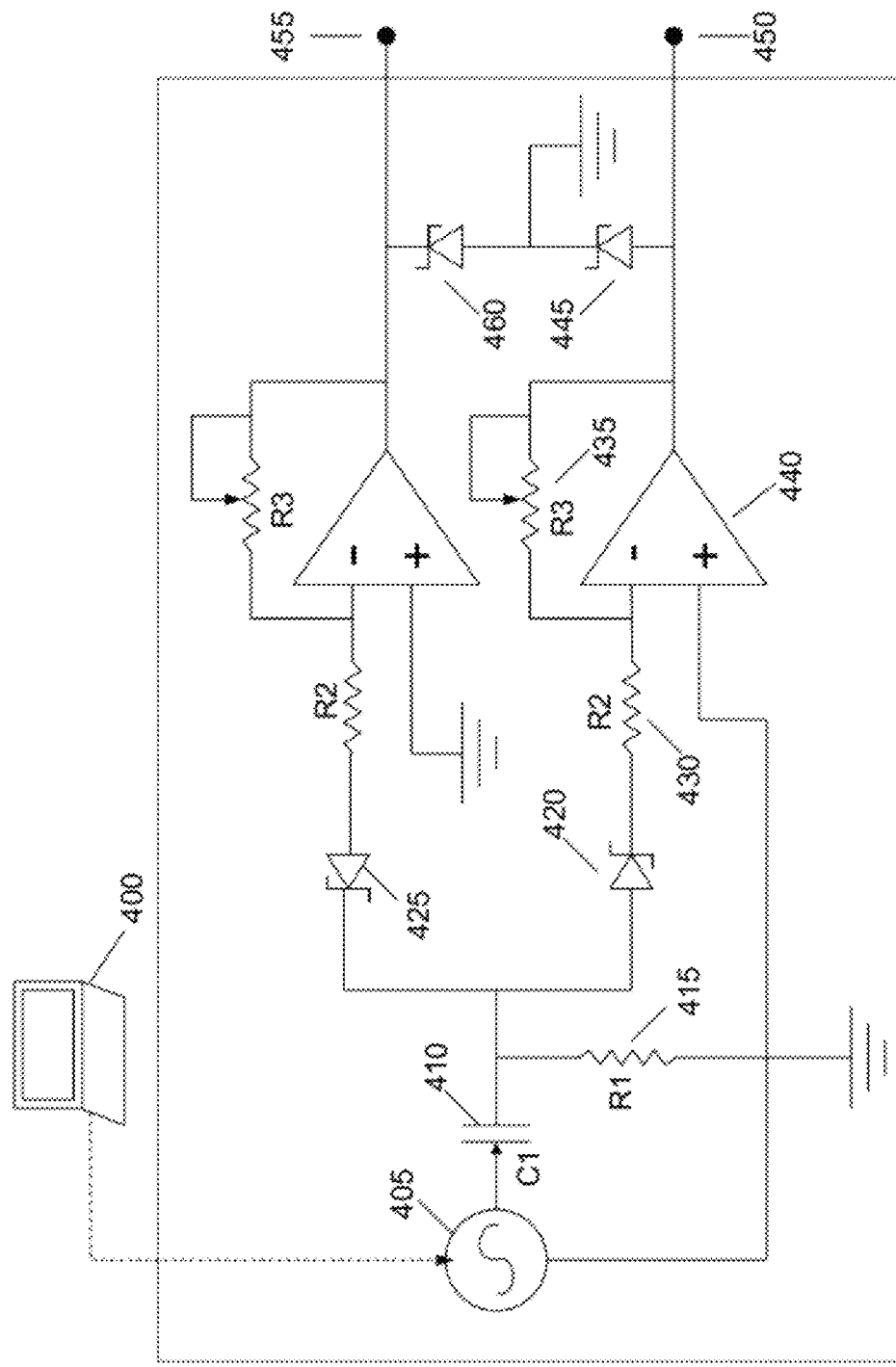
FIG. 15 illustrates a schematic diagram of a simple op amp based cranial electrical stimulation device driven by a PC based way file according to the present inventions.

FIG. 15 illustrates a schematic diagram of a simple op amp based cranial electrical stimulation device driven by a PC or any similar device capable of playing out a way file. Perhaps this is the most rudimentary yet flexible way to generate a lucid dream inducing waveform. This product realization is taken in three steps.

First, a C code program that generates a custom brain state entrainment signal is written. Sample computer C code is provided in the appendix as an example that generated the raw data associated with the plot in FIG. 1. This code had set a vector length of N=1024 in order to facilitate a Discrete Fourier Transform (DFT) based calculation of the spectral response. In practice, one would design the time domain properties as necessary and run the DFT loop to check the spectrum peak locations. A review of the output file CES_opt.dat would follow. If the realization and supporting prints and data look fine, sample size N would be modified in order to create an integer multiple of time domain signal cycles. CES_opt.dat would then be regenerated based on this modification. This step would insure phase continuity and lack of DC bias if the resulting floating point signal were recursively played.

Next, a utility function which converts raw floating point values (CES_opt.dat) at a defined sampling frequency would be leveraged to generate a binary WAV file CES_opt.wav. Such a file is decodable on a standard personal computer (PC) using generic tools such as Windows Media Player. The chosen tool is set to loop CES_opt.wav indefinitely, which drives this audio signal out of the standard audio jack of the PC.

Finally, this output signal is used to drive a simple Op Amp based amplifier that drives two electrodes. FIG. 15 demonstrates this concept. Here, PC 400 is used to drive oscillator 405 which has the functional capability of delivering the brain state entrainment signal to the ensuing parallel amplifier stages at a voltage relative to the circuits common ground. $C_1$ 410 and $R_1$ 415 are chosen to support high pass filtering with a 3 dB knee very close to 0 Hz to insure any DC bias is blocked. Schottky diode 420 is effectively a switch that transmits positive voltage signal pulses. Schottky diode 425 is effectively a switch which is open during positive voltage signal pulses and hence blocks the signal from further transmission through the circuit. Resistors $R_2$ 430 and $R_3$ 435 are chosen to deliver suitable voltage gain where $R_3$ is a potentiometer allowing fine tuning of the output signal power.

Op Amp 440 is configured in an inverting mode and delivers the amplified and inverted waveform to electrode 450. Schottky diode 445 does not conduct this waveform due to the waveform polarity. The waveform is applied to the subject via a standard strategy such as ear clips and returned via electrode 455. Schottky diode 460 conducts due to the negative waveform polarity and is returned to ground. It will be recognized by those skilled in the art that negative pulses follow a path in the mirrored gain stage of this circuit and are delivered to the subject via electrode 455 and returned via electrode 450.

It should be recognized that the first two stages of this process could easily be collapsed into a custom and commercial program that allows the user flexible choices of CES.wav signal design and fabrication.

CES Device with Offline Signal Construction and Download Feature

Figure 16:
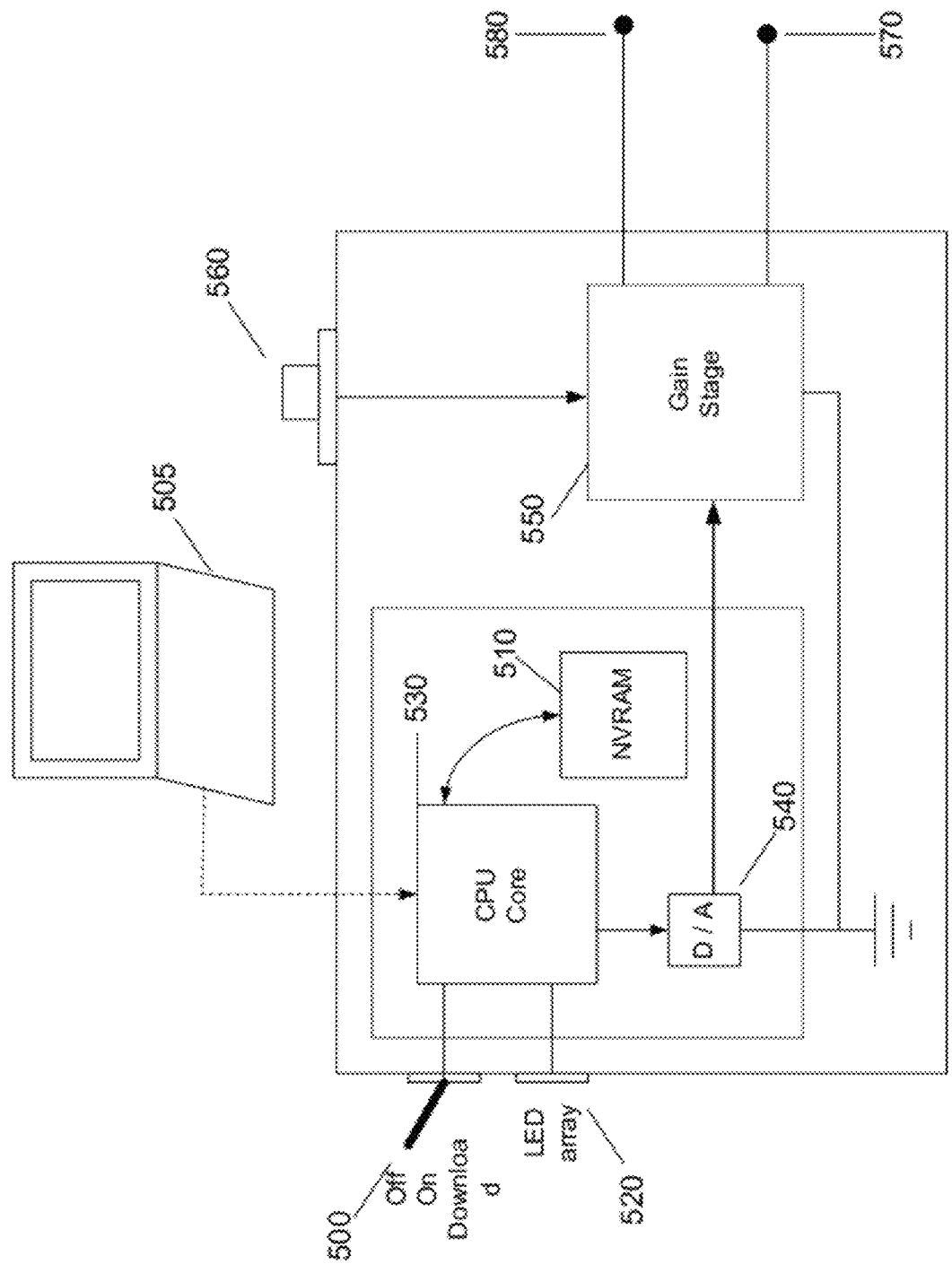
FIG. 16 illustrates a block diagram of a cranial electrical stimulation device with offline signal construction and download feature according to the present inventions.

FIG. 16 illustrates a block diagram of a cranial electrical stimulation device with offline signal construction and download feature. A cranial electrical stimulation machine realization that is potentially more convenient than that in FIG. 15 is displayed in FIG. 16. A custom piece of software is developed and designed to generate arbitrary lucid dream inducing digitally sampled signals. The physical device has three modes {off, on, download}. The device is placed in the "download" mode via a switch 500 and a simple file transfer is implemented from PC 505 to the cranial electrical stimulation device. In this download mode, the file transfer is written to non-volatile random access memory (NVRAM 510). An LED array 520 is capable of displaying one of five status messages {download ready, downloading, download error, download success, active}. In download mode, the LED initially shows "download ready". Once file transfer is commenced the LED shows "downloading" status. Finally, "download error" or "download success" is displayed based on successful file transfer and format recognition or lack thereof. In the on position, the CPU core 530 reads NVRAM and begins playing out a recursive version of the stored digital signal in a predetermined sampling frequency defined by a header provided in the initial file transfer. These synchronous digital samples drive a digital to analog converter 540 (D/A) and the reconstructed analog signal drives an analog gain stage 550 with potentiometer 560 to modify peak to peak voltage. Here, the gain stage 550 is both an amplifier and splitter which directs positive pulses to one electrode and negative pulses to the other. The gain stage terminates via electrodes 570 and 580 that deliver the lucid dream inducing cranial electrical stimulation waveform.

Figure 17:
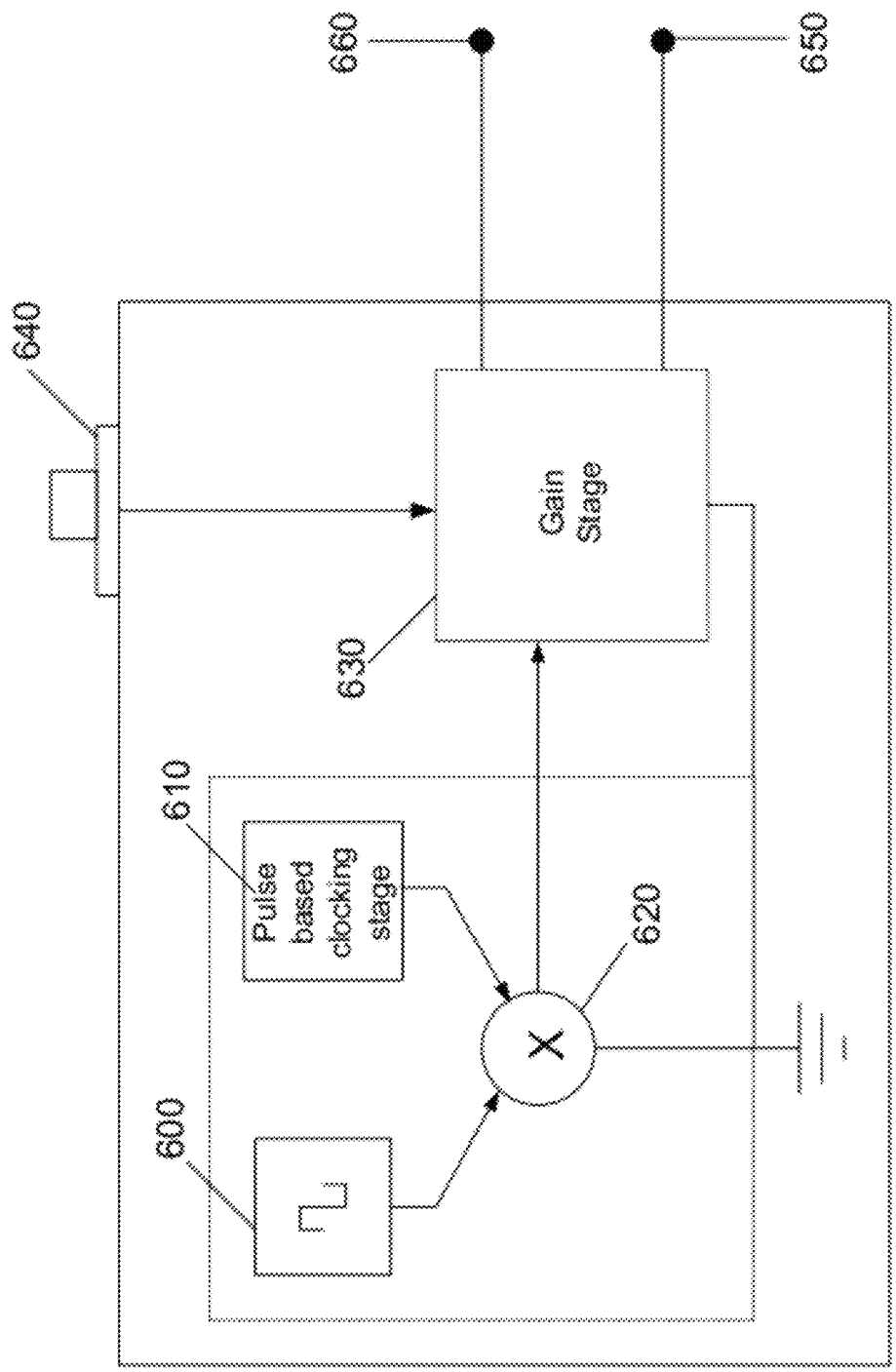
FIG. 17 illustrates a block diagram of a simple self contained device for generation of a lucid dream inducing cranial electrical stimulation waveform according to the present inventions.

Simple Self Contained Lucid Dream Inducing Cranial Electrical Stimulation Device FIG. 17 illustrates a block diagram of a simple self contained device for generation of a lucid dream inducing cranial electrical stimulation waveform. Moving on to a truly self contained cranial electrical stimulation unit we consider the device in FIG. 17. This figure is conceptual in nature but demonstrates the relative simplicity of this minimal feature design option. Here, a square wave generator 600 is designed to output the continuous 39.5 Hz square wave that serves as the desired brainstate entrainment signal envelope. A second stage 610 is designed to generate a continuous stream of pulses at 632 Hz with the desired pulse duration of 0.23734177 mS. The outputs of these devices feed a multiplier stage 620 and yields the desired time domain format of $CES_{pref}(t)$. As before, a gain stage and splitter 630 with potentiometer 640 is used to amplify the signal to yield the desired voltage and current characteristics. The resulting waveform is delivered to the subject via electrodes 650 and 660.

Self Contained Lucid Dream Inducing CES Device with All Supported Features

A device capable of supporting lucid dream inducing cranial electrical stimulation waveforms as well as all supporting features is a complex undertaking. In practice, such a device would likely rely heavily on a general purpose CPU core if the device is to support configuration and display, vibrational alarm input/output, state machine tracking and signal generation. An additional feature which a general purpose CPU based design could facilitate is a REM detector. It will be recognized based on previous discussion that the alignment of REM with the end of a CES cycle is ideal. One can easily envision several ways to implement REM detection and allowing that detection to halt the CES stimulus. For example, an external REM detection device could be designed to interface to the CES device. Such an external device would send a signal to the CES device when REM is detected in the subject. The REM detection module could rely on several existing technologies. Examples would include but are not limited to an infrared light applied to the eyelids for purpose of detecting fluctuations in the reflected signal indicative of REM, an EEG to detect REM brainwave patterns or a sensor used to detect paralysis of the exoskeletal muscles consistent with REM. Regardless of the REM detection technology used, the decision that REM has begun can be used as an input to the CES device to halt the cranial electrical stimulation immediately or in a time delayed fashion. To appreciate the complexity of this collection of requirements, consider FIG. 18.

Figure 18:
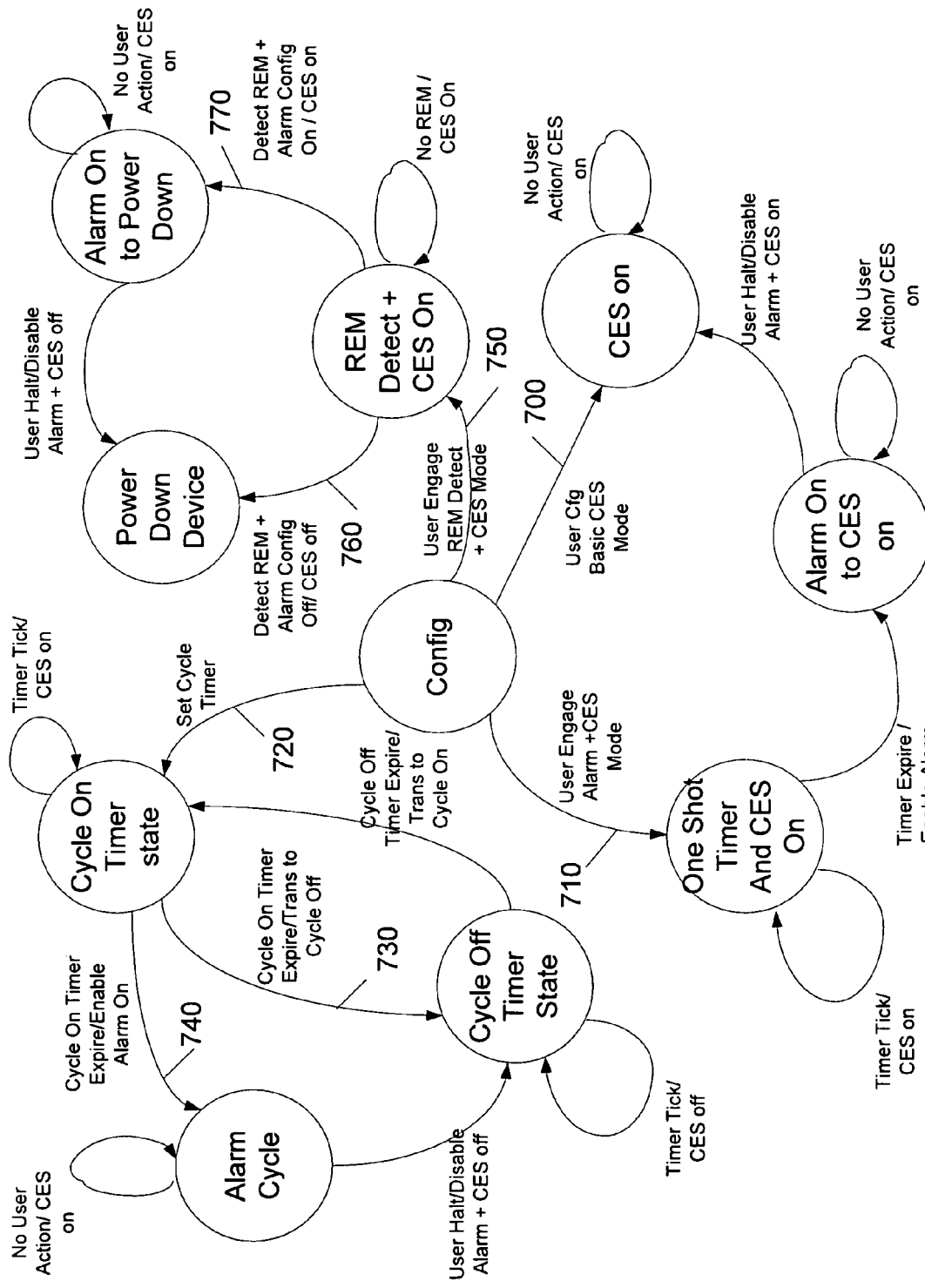
FIG. 18 illustrates a state machine diagram to implement all cited lucid dream supporting features according to the present inventions.

FIG. 18 illustrates a state machine diagram to implement all cited lucid dream supporting features. This is a state machine which implements all possible options discussed previously. Transitions are represented by the convention X/Y where X is a system operation or user input and Y represents 0 or more system transitions or outputs. Transition 700 is the basic configuration of a CES waveform with no additional features. Transition 710 corresponds to CES plus a vibrational alarm which fires at the end of a configured time duration. Transition 720 relates to the cyclic on/off mode. Within transition 720 resides the basic cycle mode option transition 730 as well as parallel transition 740 which supports the cycle on/off mode plus a vibrational alarm which fires at the end of the configured CES on duration. Transition 750 corresponds to the options with REM detection support. Logical transitions which flow from 750 are 760 and 770. Here, transition 760 corresponds to the case of REM detection halting the CES stimulus and turning off the device. Transition 770 corresponds to REM detection initiating the vibrational alarm with subsequent intervention by the user to halt the stimulus and power down the device. Note that there is an implied transition out of all states to power down the device and halt the CES stimulus.

Figure 19:
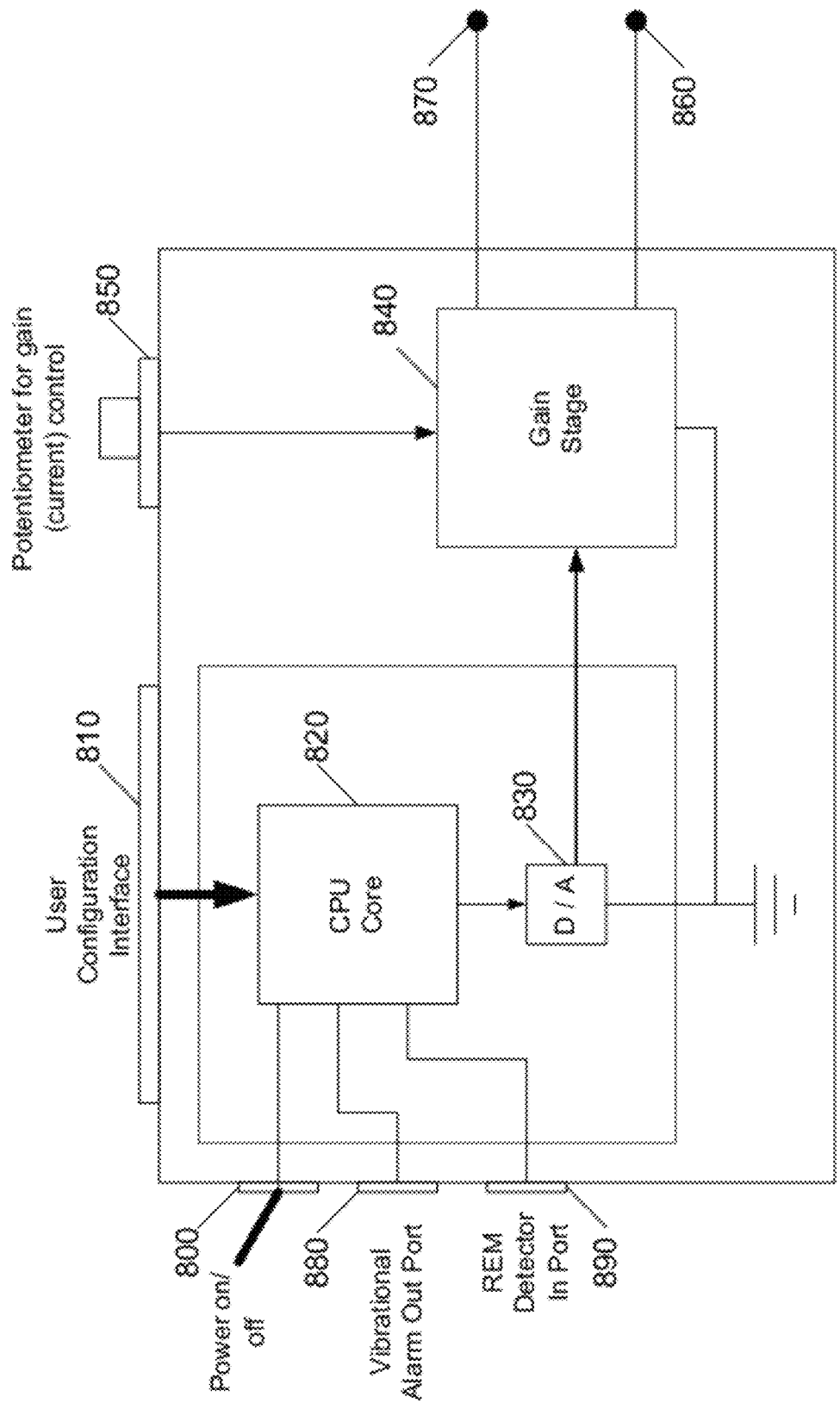
FIG. 19 illustrates a block diagram of a self contained lucid dream inducing cranial electrical stimulation device according to the present inventions.

FIG. 19 illustrates a block diagram of a self contained lucid dream inducing cranial electrical stimulation device. The state machine of FIG. 18 can be implemented on a general purpose CPU core as in FIG. 19. This self contained lucid dream inducing cranial electrical stimulation device can be described as follows. Switch 800 is used to power up or power down the device. Once on, the subject uses configuration interface 810 to program the desired mode. CPU core 820 is the module responsible for configuration storage, state machine implementation and all I/O including the digitally sampled brain state entrainment signal which is reconstructed via D/A converter 830. Block 840 is a gain and splitter stage which passes amplified positive pulses to one external electrode 860 and amplified negative pulses to the other external electrode 870. Potentiometer 850 controls the power transfer to the subject. Port 880 is used to drive an external vibrational alarm based on CPU state. Port 890 accepts a signal from an external REM detector device and is used to drive the state machine internal to the CPU core. While this figure is conceptual in nature, it is clearly a general framework capable of supporting all desired features.

Figure 20:
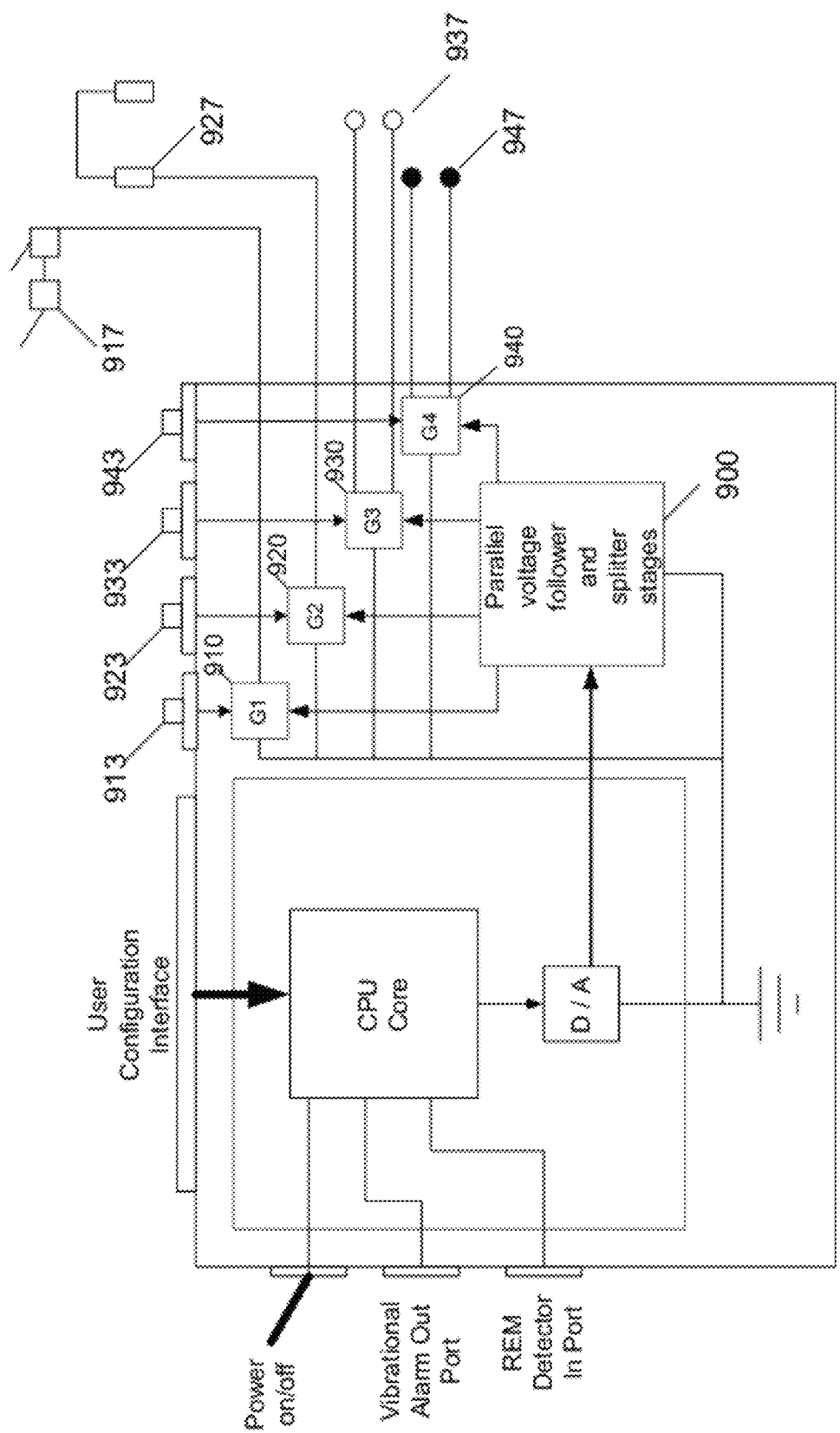
FIG. 20 illustrates a block diagram of a self contained lucid dream inducing device capable of generating one or more brain state entrainment stimuli according to the present inventions.

FIG. 20 illustrates a generalization of the device presented in FIG. 19. The generalization developed in FIG. 20 can provide any combination of four external waveform stimuli to the user via four independent transduction techniques. Here, the D/A converter feeds a parallel set of voltage follower and splitter stages 900. Each unity gain splitter stage feeds an independent gain and transduction stage. For example, one such brain state entrainment signal is provided to gain stage G1 910 controlled by potentiometer 913. The resulting stereo signal feeds a standard pair of light goggles 917. A second brain state entrainment signal is used to drive gain stage G2 920 controlled by potentiometer 923. This resulting stereo signal feeds a standard pair of stereo headphones 927. A third brain state signal is used to drive gain stage G3 930 controlled by potentiometer 933. The resulting biphasic signal feeds a transducer which converts the amplified electrical signal into a biphasic magnetic signal alternating between magnets 937. Finally, a fourth brain state entrainment signal is used to drive gain stage G4 940 controlled by potentiometer 943. This resulting biphasic signal feeds a pair of electrodes represented by 947.

The signal processing techniques disclosed herein with reference to the accompanying drawings are preferably implemented on one or more digital signal processors (DSPs) or other microprocessors. Nevertheless, such techniques could instead be implemented wholly or partially as discrete components. Further, it is appreciated by those of skill in the art that certain well known digital processing techniques are mathematically equivalent to one another and can be represented in different ways depending on choice of implementation.

Any letters designations such as (a) or (b) etc. used to label steps of any of the method claims herein are step headers applied for reading convenience and are not to be used in interpreting an order or process sequence of claimed method steps. Any method claims that recite a particular order or process sequence will do so using the words of their text, not the letter designations.

Unless stated otherwise, terms such as "first" and "second" are used to arbitrarily distinguish between the elements such terms describe. Thus, these terms are not necessarily intended to indicate temporal or other prioritization of such elements.

Although the inventions have been described and illustrated in the above description and drawings, it is understood that this description is by example only, and that numerous changes and modifications can be made by those skilled in the art without departing from the true spirit and scope of the inventions. Although the examples in the drawings depict only example constructions and embodiments, alternate embodiments are available given the teachings of the present patent disclosure. For example, other methods of brainwave entrainment at the prescribed lucid dream inducing frequency range are potential candidates for lucid dream induction assuming the timing protocol defined herein. This might include but not be limited to light, sound or a fluctuating magnetic field applied to the cranium.

APPENDIX

```
#include <stdlib.h>
#include <math.h>
#include <conio.h>
#include <stdio.h>
#define TRUE 1
#define FALSE 0
#define N 1024
#define _2PI 2.0 * 3.141592654
int     DFT(int, int, float *, float *);
void    Mag_SQ_Response(int, float *, float *, float *);
int main( )
{
   int      i, j, DFT_ret;
   float    real_data[N];
   float    imag_data[N];
   float    Mag_SQ_Resp[N];
   float    env_period_div_by_2;
   float    time_tick;
   float    sig_time_total;
   float    amplitude;
   int      thresh_adj;
   float    carrier_thresh_on;
   float    carrier_thresh_off;
   int      on_phase;
   FILE     *fileptr;
   fileptr=fopen("CES_opt.dat","w");
   sig_time_total=0;
   env_period_div_by_2=0.5/39.5;
   time_tick=1.0/19200.0;
   amplitude=15.0;
   thresh_adj=1;
   for(i=0; i<N; i++)              //main 39.5 Hz envelope
                                   signal
   {
      real_data[i]=amplitude;
      sig_time_total+=time_tick;
      if( sig_time_total >= (thresh_adj*env_period_div_by_2) )
      {
         amplitude*=-1;
         thresh_adj+=1;
      }
      imag_data[i]=0;
   }
   sig_time_total=0;
   carrier_thresh_off=1.0/632.0;
   carrier_thresh_on=0.15*carrier_thresh_off;
   thresh_adj=1;
   on_phase=1;
   for(i=0; i<N; i++)              //create modulated signal
   {
      sig_time_total+=time_tick;
      if(on_phase==1)
      {
         if( sig_time_total >=
             ( (thresh_adj-1)*carrier_thresh_off +
carrier_thresh_on) )
            on_phase=0;
      }
      else
      {
         real_data[i]=0;
         if( sig_time_total >= (thresh_adj*carrier_thresh_off) )
         {
            on_phase=1;
            thresh_adj+=1;
         }
      }
      fprintf(fileptr,"          %f; \n",real_data[i]);
   }
   DFT_ret=DFT(1, N, real_data, imag_data);
   if(DFT_ret==TRUE)
   {
      Mag_SQ_Response(N, real_data, imag_data, Mag_SQ_Resp);
      printf("\n\n");
      for(i=0, j=0; i<30; i++, j++)
      {
```

APPENDIX-continued

```
         printf("%d      %f \n", i, (float)Mag_SQ_Resp[i] );
         if(j==10)
         {
            j=0;
            getch( );
         }
      }
   }
   fclose(fileptr);
   return 0;
}
int DFT(int dir, int m, float *x1, float *y1)
{
   long     i,k;
   float    arg;
   float    cosarg, sinarg;
   float    *x2=NULL, *y2=NULL;
   x2 = malloc( m*sizeof(float) );
   y2 = malloc( m*sizeof(float) );
   if (x2 == NULL || y2 == NULL)
      return(FALSE);
   for (i=0; i<m; i++)
   {
      x2[i] = 0;
      y2[i] = 0;
      arg = - dir * _2PI * (float)i / (float)m;
      for (k=0; k<m; k++)
      {
         cosarg = cos(k * arg);
         sinarg = sin(k * arg);
         x2[i] += (x1[k] * cosarg - y1[k] * sinarg);
         y2[i] += (x1[k] * sinarg + y1[k] * cosarg);
      }
   }
   if (dir == 1)
   {
      for (i=0; i<m; i++)
      {
         x1[i] = x2[i] / (float)m;
         y1[i] = y2[i] / (float)m;
      }
   }
   else
   {
      for (i=0; i<m; i++)
      {
         x1[i] = x2[i];
         y1[i] = y2[i];
      }
   }
   free(x2);
   free(y2);
   return(TRUE);
}
void Mag_SQ_Response(int L, float *X1, float *X2, float *M)
{
   int i;
   for(i=0; i<L; i++)
      M[i]= pow(X1[i],2) + pow(X2[i],2);
}
```

What is claimed is:

1. An apparatus that induces a lucid dream in the brain of a subject, comprising:
   a circuit that generates a brain state entrainment signal sufficient to cause a lucid dream in the brain of the subject by entrainment; and
   a transducer operatively coupled to receive the brain state entrainment signal from the circuit and apply a waveform to the subject while the subject is awake,
   wherein the brain state entrainment signal has a ratio metric characteristic wherein a ratio of signal energy in the band from 34.5 Hz to 44.5 Hz divided by signal energy in the band from 20 Hz to 100 Hz is 0.25 or greater for any time window of 0.1 seconds along a contiguous moving train of such windows.

2. An apparatus according to claim 1, wherein the waveform applied to the subject by the transducer is chosen from the group consisting of an electrical waveform, a light waveform, a sound waveform and a magnetic waveform.

3. An apparatus according to claim 2, wherein the brain state entrainment signal has a frequency in a range of 34.5 Hz to 44.5 Hz.

4. An apparatus according to claim 3, wherein the brain state entrainment signal has a frequency in a range of 37.5 Hz to 41.5 Hz.

5. An apparatus according to claim 4, wherein the brain state entrainment signal has a frequency of 39.5 Hz.

6. An apparatus according to claim 2, wherein the waveform applied to the subject by the transducer comprises cranial electrical stimulation.

7. An apparatus according to claim 6, wherein the circuit uses the brain state entrainment signal to modulate a carrier wave of a frequency higher than an envelope of the brain state entrainment signal.

8. An apparatus according to claim 7, wherein the brain state entrainment signal has an envelope of 37.5 Hz to 41.5 Hz.

9. An apparatus according to claim 8, wherein the carrier wave has a frequency of 632 Hz.

10. An apparatus according to claim 9, wherein the carrier wave has a duty cycle less than 100%.

11. An apparatus according to claim 10, wherein the duty cycle of the carrier wave is less than 50%.

12. An apparatus according to claim 8, wherein the carrier wave has a duty cycle less than 100%.

13. An apparatus according to claim 12, wherein the duty cycle of the carrier wave is a duty cycle of 15%.

14. An apparatus according to claim 1, wherein the circuit generates the brain state entrainment signal for no less than a predetermined duration of time.

15. An apparatus according to claim 14, wherein the circuit generates the brain state entrainment signal for no less than a duration of time of 45 minutes.

16. An apparatus according to claim 1, wherein the circuit ends the brain state entrainment signal during rapid eye movement sleep.

17. An apparatus according to claim 16, wherein the circuit ends the brain state entrainment signal during a beginning portion of the rapid eye movement sleep.

18. An apparatus according to claim 1, wherein the apparatus further comprises a timer operatively coupled to the circuit to diminish or end the brain state entrainment signal in response to the timer.

19. An apparatus according to claim 18, wherein the apparatus further comprises an alarm to awaken the subject around the time when the brain state entrainment signal has been diminished or ended.

20. An apparatus according to claim 19, wherein the apparatus further comprises another timer operatively coupled to the circuit to control a duration of time to diminish or end the brain state entrainment signal.

21. An apparatus according to claim 1, wherein the circuit sequentially generates the brain state entrainment signal to repeat other lucid dream attempts.

22. A method of inducing a lucid dream in a subject, comprising the steps of:
(a) generating a brain state entrainment signal using a circuit
(b) applying a waveform to the subject using a transducer based on the brain state entrainment signal in order to create a suppression of natural electro-chemical activity in the brain associated with an alert mental state and awareness; and
(c) removing the waveform from the subject after an entrainment session to create a subsequent rebound effect of the electro-chemical signature in the subjects brain associated with an alert mental state and awareness ha order to induce a lucid dream, wherein the waveform generated in said step (b) has a ratio metric characteristic wherein a ratio of waveform energy in the band from 34.5 Hz to 44.5 Hz divided by waveform energy in the band from 20 Hz to 100 Hz is 0.25 or greater for any time window of 0.1 seconds along a contiguous moving train of such windows.

23. A method of inducing a lucid dream according to claim 22, wherein the brain state entrainment signal generated in said step (a) is of a kind sufficient to cause a lucid dream in the brain of the subject.

24. A method of inducing a lucid dream according to claim 22, wherein the waveform applied in said step (b) is removed in said step (c) after a duration of time sufficient to prepare the subject to have the lucid dream.

25. A method of inducing a lucid dream according to claim 22, wherein the removal of the waveform in said step (c) comprises one of ending or diminishing.

26. A method of inducing a lucid dream according to claim 22, wherein the waveform applied in said step (b) is chosen from the group consisting of an electrical waveform, a light waveform, a sound waveform and a magnetic waveform.

27. A method of inducing a lucid dream according to claim 26, wherein the waveform applied in said step (b) comprises cranial electrical stimulation.

28. A method of inducing a lucid dream according to claim 22, wherein the waveform is applied in said step (b) for no less than a predetermined duration of time.

29. A method of inducing a lucid dream according to claim 28, wherein the waveform is applied in said step (b) for no less than a duration of time of 45 minutes.

30. A method of inducing a lucid dream according to claim 28, further comprising the step of
(d) running a timer to measure the predetermined duration of time; and
(e) alarming the subject at the end of the predetermined duration of time to wake the subject.

31. A method of inducing a lucid dream according to claim 22, wherein said step (c) of removing comprises removing the waveform from the subject during rapid eye movement sleep.

32. A method of inducing a lucid dream according to claim 31, wherein said step (c) of removing the waveform during rapid eye movement sleep removes the waveform during a beginning portion of the rapid eye movement sleep.

33. A method of inducing a lucid dream according to claim 22, wherein the brain state entrainment signal generated in step (a) modulates a carrier wave of a higher frequency than an envelope of the brain state entrainment signal.

34. A method of inducing a lucid dream according to claim 33, wherein the brain state entrainment signal generated in said step (a) has an envelope of 37.5 Hz to 41.5 Hz.

35. A method of inducing a lucid dream according to claim 34, wherein the carrier wave has a duty cycle less than 100%.

36. A method of inducing a lucid dream according to claim 34, wherein the duty cycle of the carrier wave is a 15% duty cycle.

37. A method of inducing a lucid dream according to claim 34, wherein the carrier wave has a frequency of 632 Hz.

38. A method of inducing a lucid dream according to claim 37, wherein the carrier wave has a duty cycle less than 50%.

39. A method of inducing a lucid dream according to claim 38, wherein the duty cycle of the carrier wave is a 15% duty cycle.

40. A method of inducing a lucid dream according to claim 22, wherein the brain state entrainment signal generated in said step (a) has a frequency in a range of 34.5 Hz to 44.5 Hz.

41. A method of inducing a lucid dream according to claim 40, wherein the brain state entrainment signal generated in said step (a) has a frequency in a range of 37.5 Hz to 41.5 Hz.

42. A method of inducing a lucid dream according to claim 41, wherein the brain state entrainment signal generated in said step (a) has a frequency of 39.5 Hz.

43. A method of inducing a lucid dream according to claim 22, further comprising the step of (d) repeating steps (a), (b) and (c) to repeat other lucid dream attempts.

\* \* \* \* \*